(12) United States Patent
Taki et al.

(10) Patent No.: US 7,876,030 B2
(45) Date of Patent: Jan. 25, 2011

(54) ULTRASONIC TRANSDUCER WHICH IS EITHER CRIMPED OR WELDED DURING ASSEMBLY

(75) Inventors: Hideaki Taki, Ise (JP); Wataru Kimura, Ise (JP); Noritaka Yoshida, Ibaraki (JP); Naohito Sato, Kasugai (JP); Mitsugu Onoda, Nagoya (JP); Hiroyuki Kawaji, Konan (JP)

(73) Assignee: NGK Spark Plug Co., Ltd., Aichi (JP)

( * ) Notice: Subject to any disclaimer, the term of this patent is extended or adjusted under 35 U.S.C. 154(b) by 220 days.

(21) Appl. No.: 12/207,539

(22) Filed: Sep. 10, 2008

(65) Prior Publication Data

US 2009/0066192 A1  Mar. 12, 2009

(30) Foreign Application Priority Data

Sep. 11, 2007  (JP) .................... P2007-235724
Sep. 11, 2007  (JP) .................... P2007-235725
Jul. 29, 2008  (JP) .................... P2008-194433

(51) Int. Cl.
*H01L 41/04* (2006.01)
*H01L 41/08* (2006.01)

(52) U.S. Cl. ............... 310/354; 310/323.12; 310/325

(58) Field of Classification Search ............ 310/323.12, 310/325, 334
See application file for complete search history.

(56) References Cited

U.S. PATENT DOCUMENTS

| 3,931,549 A |   | 1/1976 | Berns |
| 4,169,984 A | * | 10/1979 | Parisi ................. 310/325 |
| 4,315,428 A |   | 2/1982 | Stuivenwold |
| 4,850,534 A | * | 7/1989 | Takahashi et al. ........ 310/325 |
| 6,274,963 B1 |   | 8/2001 | Estabrook |
| 6,498,421 B1 | * | 12/2002 | Oh et al. ............. 310/323.12 |
| 7,728,489 B2 | * | 6/2010 | Heinz et al. ............ 310/325 |

FOREIGN PATENT DOCUMENTS

| JP | 2003-199195 A | 7/2003 |
| WO | 9702720 A1 | 1/1997 |
| WO | 0062688 A1 | 10/2000 |

* cited by examiner

*Primary Examiner*—J. SanMartin
(74) *Attorney, Agent, or Firm*—Sughrue Mion, PLLC

(57) ABSTRACT

An ultrasonic transducer includes: piezoelectric elements; a pair of clamping members which clamp said piezoelectric elements; and a cover member which is crimped to at least one of said pair of clamping members in a state where said cover member cooperates with said pair of clamping members to surround said piezoelectric elements.

14 Claims, 21 Drawing Sheets

ULTRASONIC TRANSDUCER WHICH IS EITHER CRIMPED OR WELDED DURING ASSEMBLY

FIELD OF THE INVENTION

The present invention relates to an ultrasonic transducer which generates ultrasonic vibration by electrical distortion of piezoelectric elements, and a method of producing such a transducer.

BACKGROUND OF THE INVENTION

A Langevin type ultrasonic transducer having a configuration in which a stack unit of piezoelectric elements that are integrally sintered is fitted into a recess formed in a metal-made vibration block has been proposed (for example, see Japanese Patent No. 3,914,050).

In the ultrasonic transducer disclosed in Japanese Patent No. 3,914,050, a screw hole (female thread) is formed in the inner wall of the recess of the vibration block, and a bolt is fastened to the screw hole, whereby the stack unit of piezoelectric elements is fixed to the vibration block.

Furthermore, a handpiece for surgical operation incorporating an ultrasonic transducer having a structure in which, for example, a stack type piezoelectric member housed in a recess of a housing is fastened by a horn on which a male thread is formed is known (for example, see JP-A-2004-160081).

SUMMARY OF THE INVENTION

However, such an ultrasonic transducer has the configuration in which the stack unit of piezoelectric elements is fixed by screwing as described above, and hence a region for forming a thread structure must be ensured in a radial direction of the product (the body of the ultrasonic transducer). Namely, the fixation by screwing restricts the size of the piezoelectric elements or the product body, and, therefore, causes miniaturization of the product, the increase of the output power of the product by applying large-diameter piezoelectric elements, and the like, to be impeded. In the field of medical application, particularly, it is strongly requested to develop an ultrasonic transducer which is miniaturized, and which has a small diameter. Under these circumstances, consequently, there is a request for configuring an ultrasonic transducer without using a thread structure as far as possible.

Moreover, the holding force of holding (clamping) the piezoelectric elements to the inside of an ultrasonic transducer such as described above functions as one of the elements affecting the vibration performance of the ultrasonic transducer itself. In an ultrasonic transducer having a structure which is assembled by fastening a screw to a piezoelectric element side as in Japanese Patent No. 3,914,050 and JP-A-2004-160081, however, the friction force generated during the work of fastening the screw acts as an cause of impeding the work, so that the work of installing the piezoelectric elements with an adequate holding (clamping) force is relatively difficult to perform. In the ultrasonic transducer having the structure in which a screw is fastened to a piezoelectric element side, moreover, there is a possibility that, due to torsional stress acting on the piezoelectric elements or the like, the positions of the piezoelectric elements are deviated from predetermined designed positions, thereby causing the vibration characteristics of the ultrasonic transducer to be dispersed. Furthermore, there are fears such as that, because of the above-mentioned stress in the torsional direction, mechanical stress which is larger than an allowable level is applied to the piezoelectric elements.

The invention has been conducted in order to solve the problems. It is an object of the invention to provide an ultrasonic transducer in which application of torsional stress and the like to piezoelectric elements can be suppressed, the vibration characteristics can be prevented from being dispersed, and miniaturization and increase of the output power are enabled, and also a method of producing such an ultrasonic transducer.

In order to attain the object, in a first aspect of the invention, the ultrasonic transducer is characterized in that the ultrasonic transducer includes: piezoelectric elements; a pair of clamping members which clamp the piezoelectric elements; and a cover member which is crimped to at least one of the pair of clamping members in a state where the cover member cooperates with the pair of clamping members to surround the piezoelectric elements.

In the first aspect of the invention, namely, the cover member is crimped between the pair of clamping members which clamp the piezoelectric elements, and hence the piezoelectric elements can be installed as internal components (without daringly using a thread structure). Therefore, it is possible to eliminate the necessity of ensuring a region for forming a thread structure in the product body (the body of the ultrasonic transducer), and the like. Consequently, according to the first aspect of the invention, the degree of freedom in selection of the sizes of the piezoelectric elements and the product body is enhanced, and hence it is possible to realize miniaturization of the ultrasonic transducer, increase of the output power of the ultrasonic transducer due to employment of piezoelectric elements having a relatively large size, etc.

In the first aspect of the invention, moreover, individual members can be joined together by crimping without using a thread structure and the like as far as possible. When crimping is performed while applying, for example, an adequate load from the both sides of the pair of clamping members, therefore, the piezoelectric elements can be installed between the clamping members by an adequate holding (clamping) force without applying torsional stress to the piezoelectric elements. According to the first aspect of the invention, consequently, the piezoelectric elements can be installed by an adequate holding force while suppressing positional deviation during installation of the piezoelectric elements, and hence the vibration characteristics of the ultrasonic transducer can be prevented from being dispersed. Moreover, breakage of the piezoelectric elements and the like caused by mechanical stress can be prevented from occurring.

In the first aspect of the invention, in the case of joining by crimping, to-be-joined portions are not required to be heated and melted at a high temperature unlike the case where, for example, welding is used. Therefore, the degree of freedom in selection of the materials of the clamping members and the cover member can be enhanced, and welding apparatuses which are relatively expensive are not required to be installed. Consequently, it is possible to improve the productivity of the ultrasonic transducer.

In the first aspect of the invention, the method of producing an ultrasonic transducer is characterized in that the method has: a member placing step of, while a pair of clamping members are placed at positions where piezoelectric elements are clamped from both sides, placing a cover member at a position where the cover member cooperates with the pair of clamping members to surround the piezoelectric elements; and a crimping step of crimping the cover member to at least one of the pair of clamping members in a sate where the piezoelectric elements are pressed through the pair of clamping members which are placed in the member placing step.

According to the first aspect of the invention, it is possible to provide an ultrasonic transducer in which application of torsional stress and the like to piezoelectric elements can be suppressed, the vibration characteristics can be prevented from being dispersed, miniaturization and increase of the output power are enabled, and the productivity can be improved, and also a method of producing such an ultrasonic transducer.

In order to attain the object, in a second aspect of the invention, the ultrasonic transducer is characterized in that the ultrasonic transducer includes: piezoelectric elements; a pair of clamping members which clamp the piezoelectric elements; and a cover member which is welded to the pair of clamping members while surrounding the piezoelectric elements interposed between the pair of clamping members.

In the second aspect of the invention, the pair of clamping members which clamp the piezoelectric elements are welded to each other through the cover member without using a thread structure, and hence it is possible to eliminate the necessity of ensuring a region for forming the thread structure in the product body (the body of the ultrasonic transducer), and the like. According to the second aspect of the invention, consequently, the degree of freedom in selection of the sizes of the piezoelectric elements and the product body is enhanced, and hence it is possible to realize miniaturization of the ultrasonic transducer, increase of the output power of the ultrasonic transducer due to employment of piezoelectric elements having a relatively large size, etc.

In the second aspect of the invention, moreover, welding is employed in joining of individual members without using a thread structure as described above. When a process such as that the welding is performed while applying, an adequate load from the both sides of the pair of clamping members is conducted, therefore, torsional stress is not applied to the piezoelectric elements, and the piezoelectric elements can be installed between the clamping members by an adequate holding (clamping) force. According to the second aspect of the invention, consequently, the piezoelectric elements can be installed by an adequate holding force while suppressing positional deviation during installation of the piezoelectric elements, and hence the vibration characteristics can be prevented from being dispersed. Moreover, breakage of the piezoelectric elements and the like caused by mechanical stress can be prevented from occurring.

In the second aspect of the invention, the method of producing an ultrasonic transducer is characterized in that the method has: a member placing step of placing a cover member at a position where the cover member surrounds piezoelectric elements, and placing a pair of clamping members at positions where the cover member and the piezoelectric elements are clamped from both sides; and a welding step of welding the pair of clamping members to the cover member in a sate where the piezoelectric elements are pressed through the pair of clamping members which are placed in the member placing step.

According to the second aspect of the invention, it is possible to provide an ultrasonic transducer in which generation of torsional stress and the like that may be applied to piezoelectric elements can be suppressed, the vibration characteristics can be prevented from being dispersed, and miniaturization and increase of the output power are enabled, and also a method of producing such an ultrasonic transducer.

Figure 1:
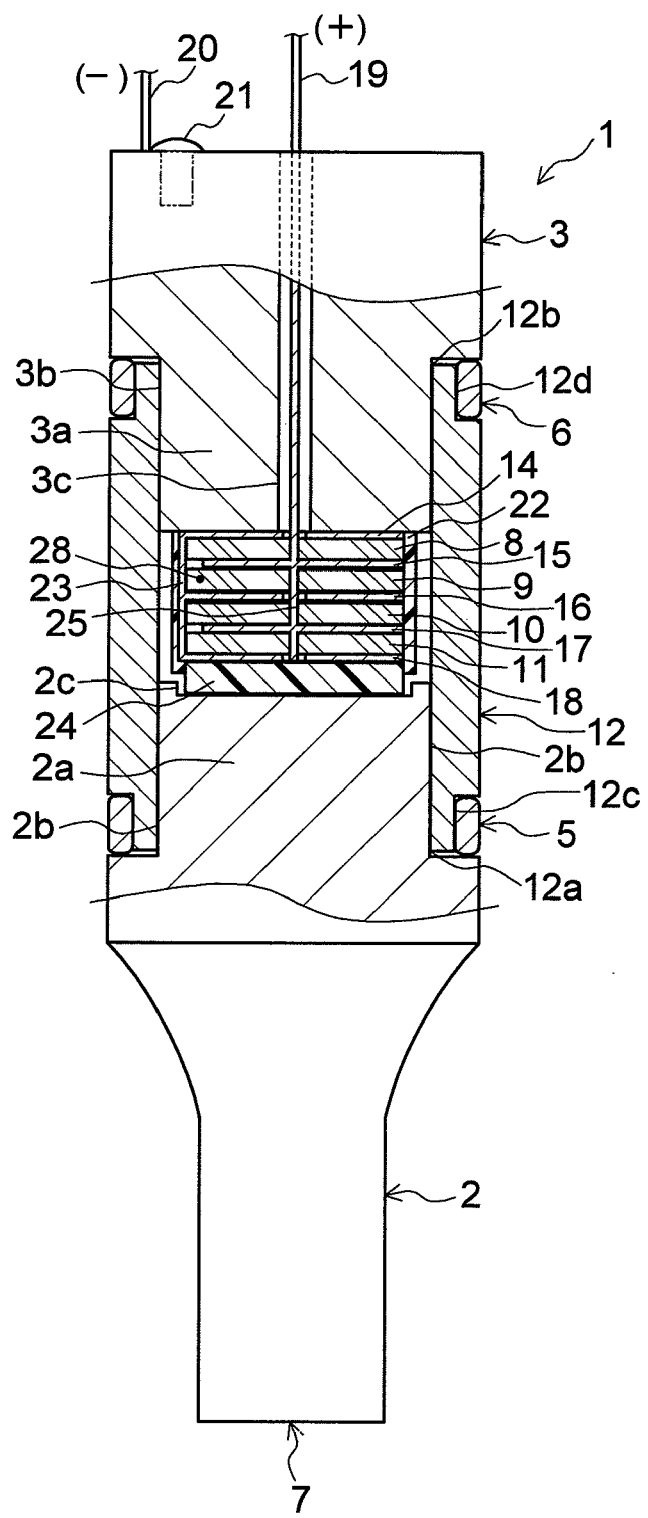
FIG. 1 is a front view showing in partially section an ultrasonic transducer of a first embodiment of the invention.

DESCRIPTION OF REFERENCE NUMERALS AND SIGNS 1, 1', 31, 31', 41, 41', 51, 51', 71, 71', 81 . . . ultrasonic transducer, 2, 32, 42, 82 . . . front plate, 2a, 82a . . . insertion portion of front plate, 2b, 3b, 32b, 33b . . . root portion of insertion portion, 3, 33, 53, 83 . . . back plate, 3a, 83a . . . insertion portion of back plate, 5, 6 . . . crimp ring, 7, 93 . . . vibration radiating surface, 8, 9, 10, 11, 88, 89, 90, 91 . . . piezoelectric element, 12, 34, 92, 920 . . . side plate, 12a, 12b, 92a, 92b . . . opening portion, 12c, 12d . . . thinned portion, 28, 100 . . . piezoelectric element unit, 42a, 53a . . . cover portion, 72, 73 . . . buffer member, 74 . . . heat shrinkable tube, 82b . . . male thread, 83b . . . step portion, 83e . . . edge portion, 92c, 92d . . . peripheral edge portion, 92e . . . female thread, 92f . . . thinned portion, 99 . . . short-circuit preventing layer, 2d . . . step portion of front plate, 3d . . . step portion of back plate, 5a, 6a . . . welded portion, 12e, 12f . . . peripheral edge portion, 29 . . . laser illuminating device, 32c, 32d . . . rib-like projection, 35, 36 . . . to-be-welded portion.

DETAILED DESCRIPTION OF THE INVENTION

Hereinafter, the best mode for carrying out the invention will be described.

First and Second Embodiments

Figure 2:
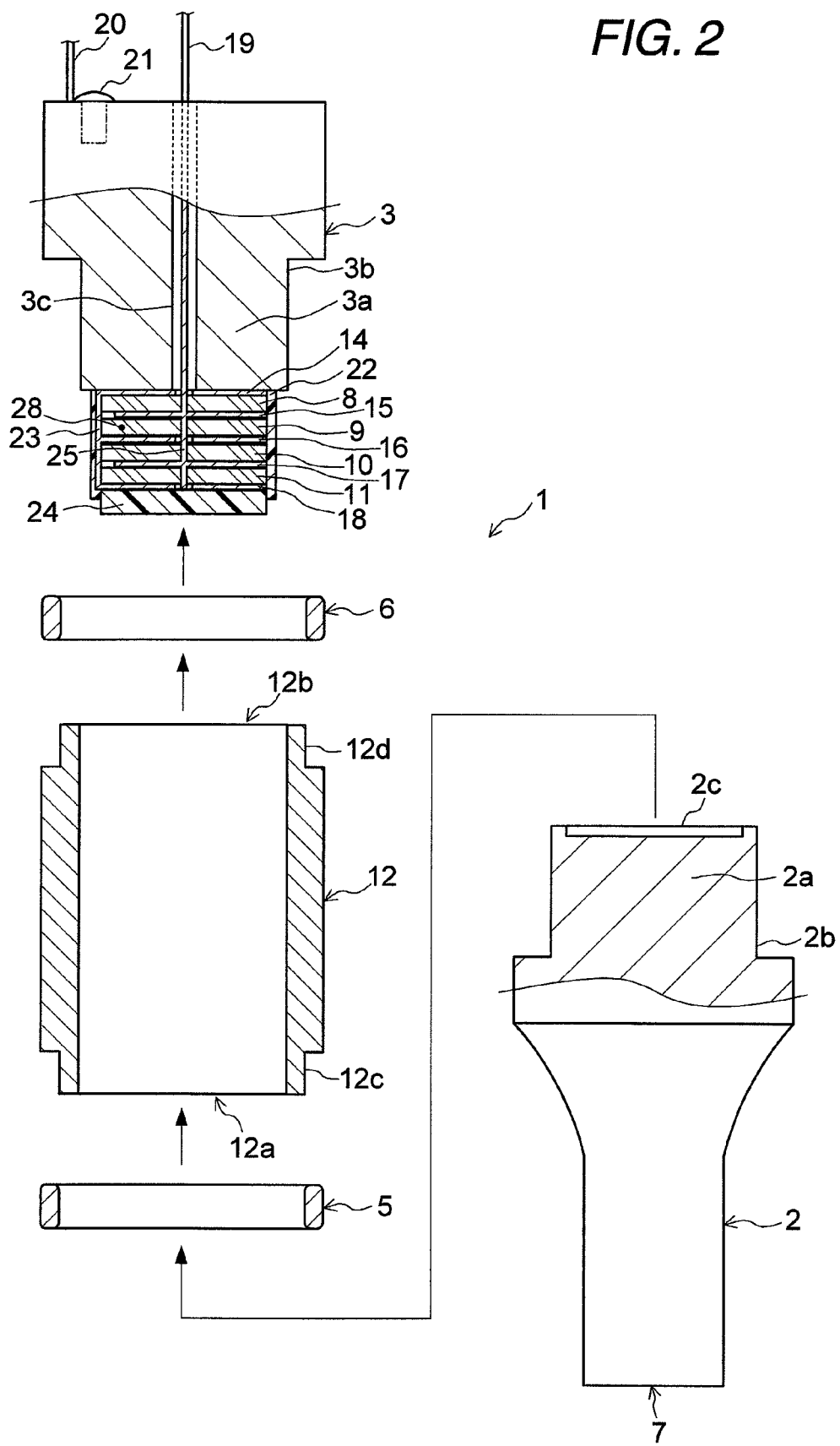
FIG. 2 is an exploded view showing partial components of the ultrasonic transducer of FIG. 1.
Figure 3:
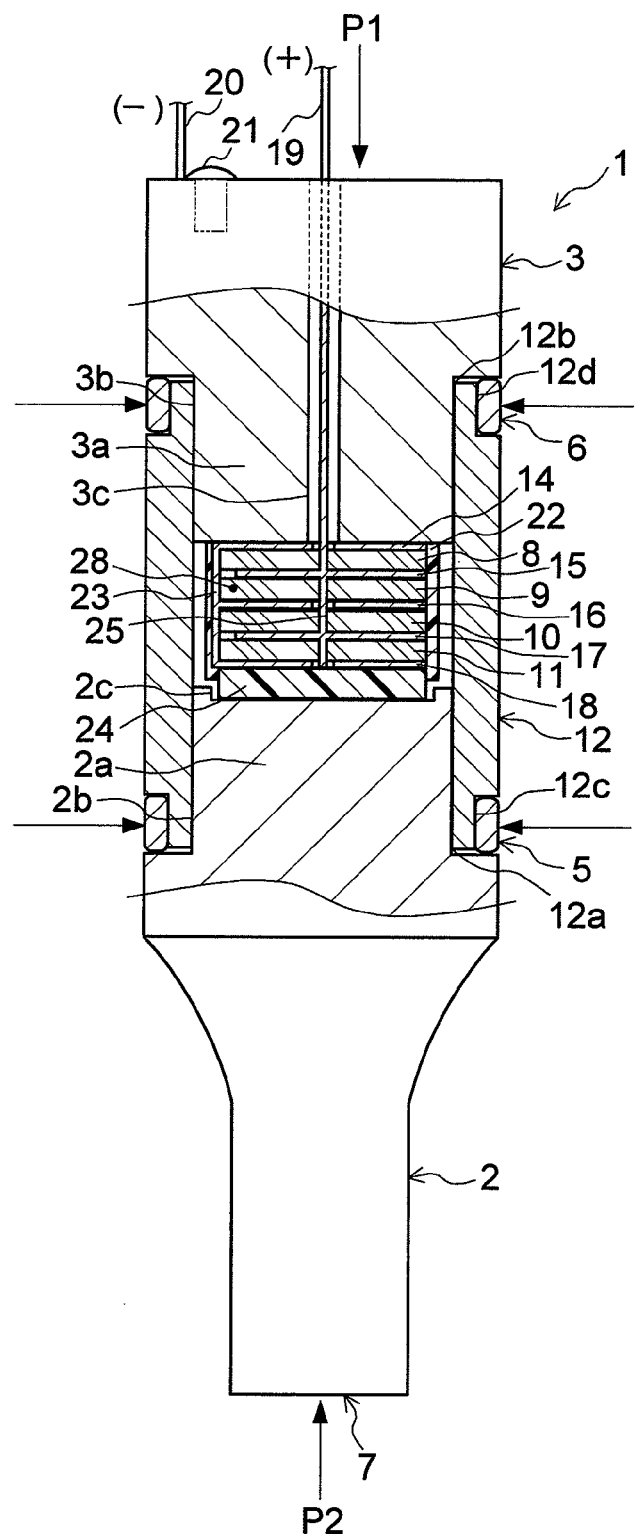
FIG. 3 is a view illustrating a method of producing the ultrasonic transducer of FIG. 1.

FIG. 1 is a front view showing in partially section an ultrasonic transducer 1 of a first embodiment of the invention, and FIG. 2 is an exploded view showing partial components of the ultrasonic transducer 1. FIG. 3 is a view illustrating a method of producing the ultrasonic transducer 1.

Figure 17:
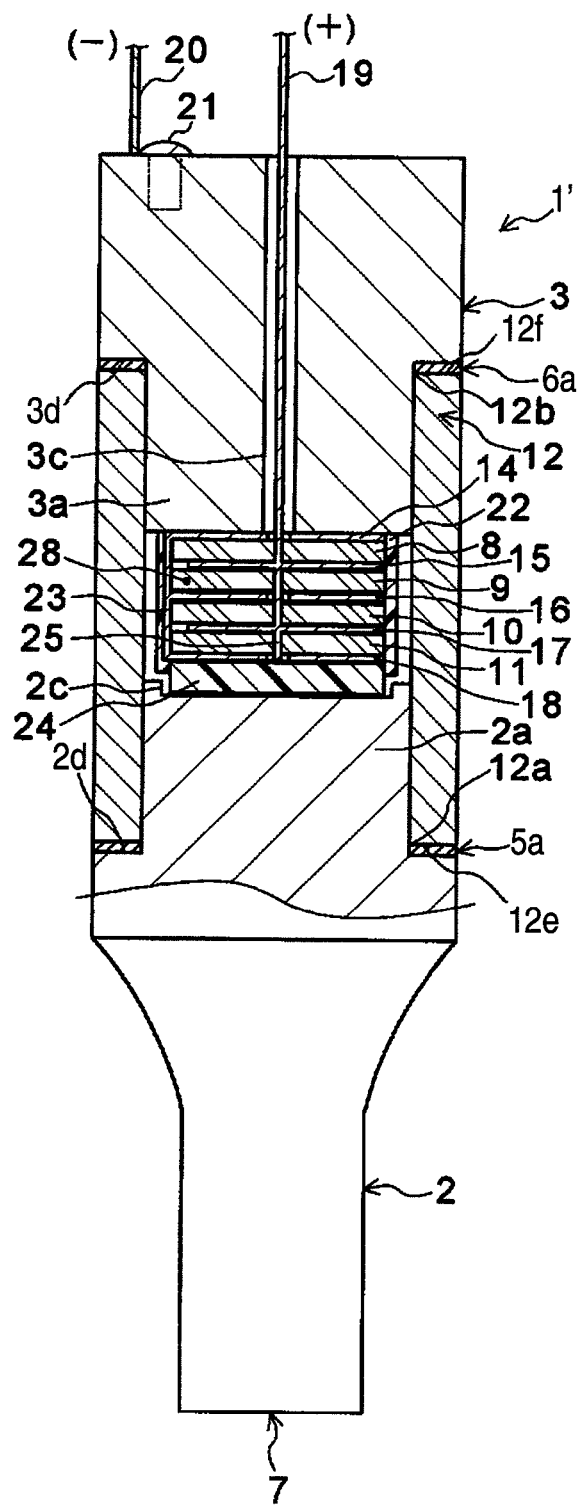
FIG. 17 is a front view showing in partially section an ultrasonic transducer of a second embodiment of the invention.
Figure 18:
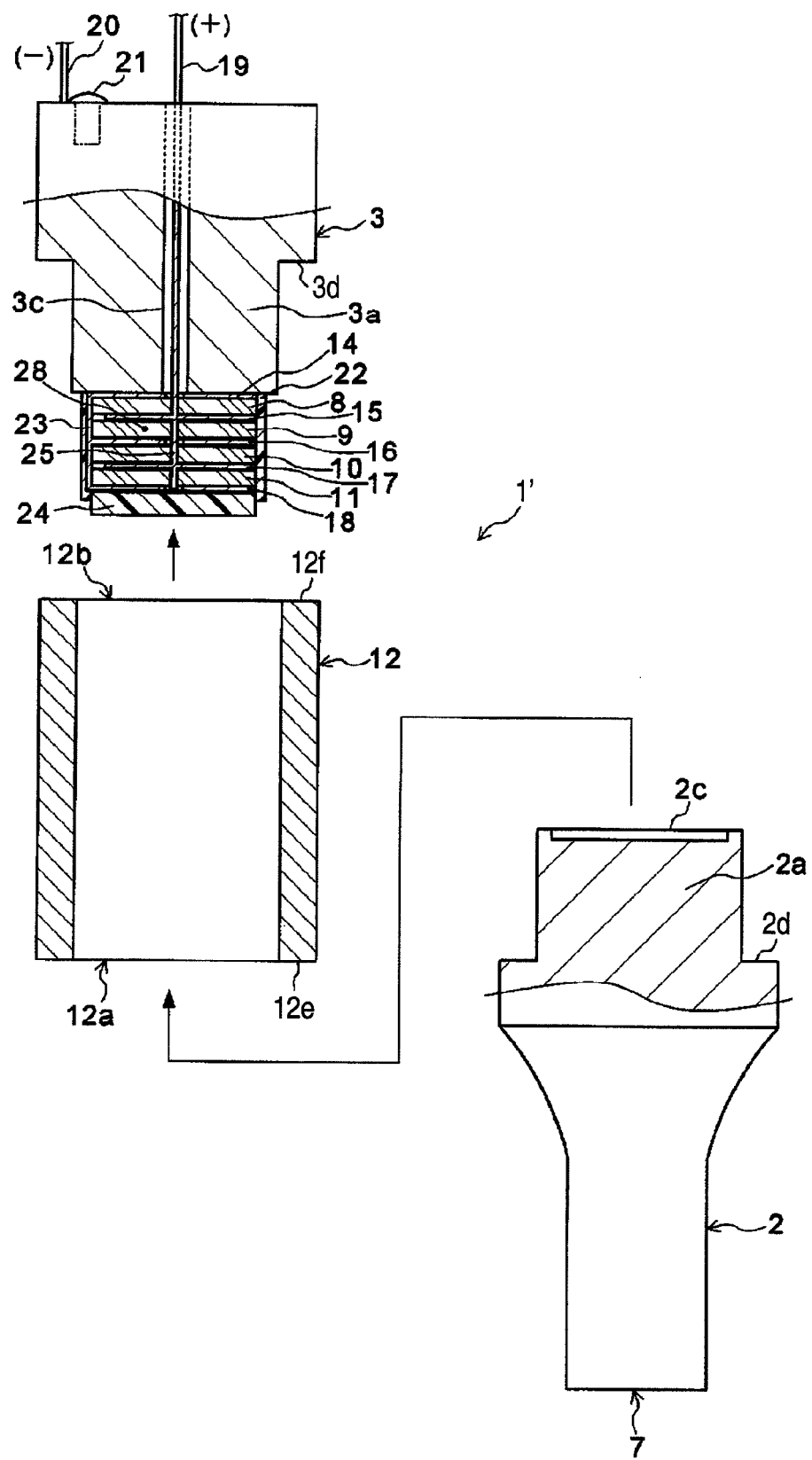
FIG. 18 is an exploded view showing partial components of the ultrasonic transducer of FIG. 17.
Figure 19:
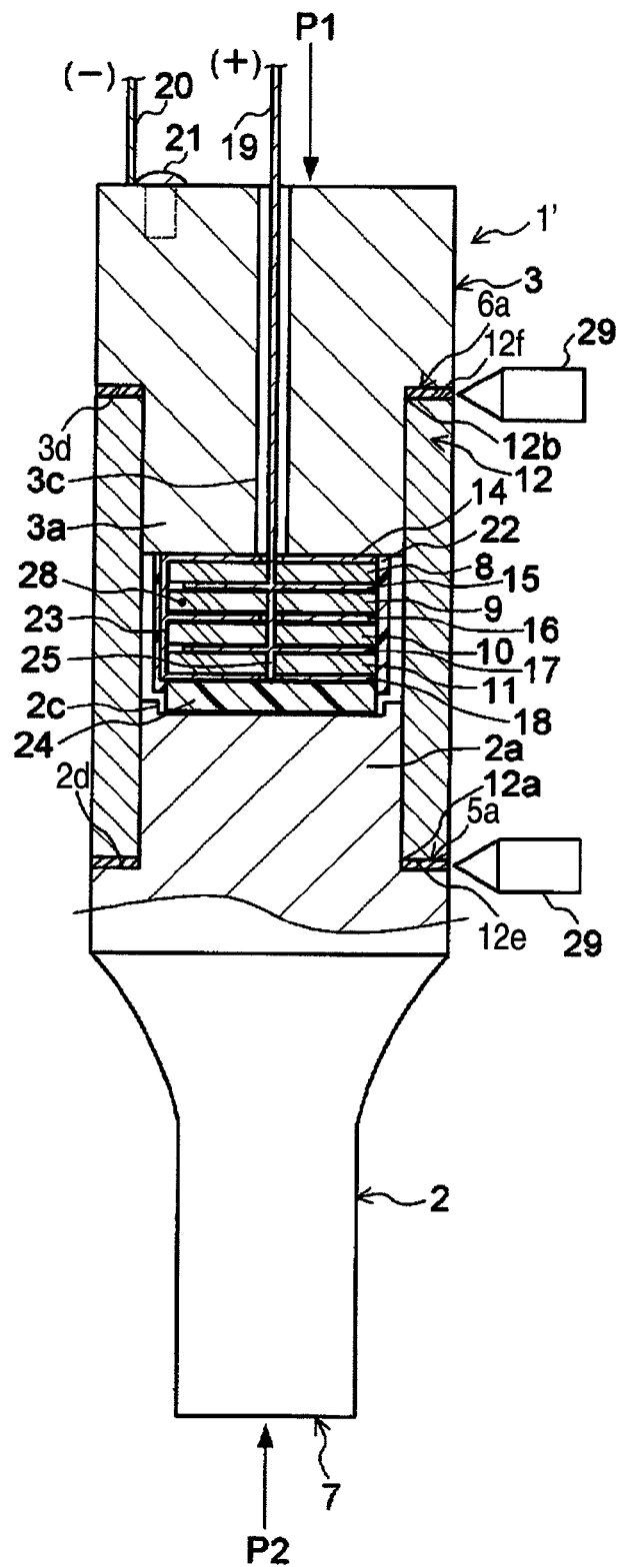
FIG. 19 is a view illustrating a method of producing the ultrasonic transducer of FIG. 17.

FIG. 17 is a front view showing in partially section an ultrasonic transducer 1' of a second embodiment of the invention, and FIG. 18 is an exploded view showing partial components of the ultrasonic transducer 1'. FIG. 19 is a view illustrating a method of producing the ultrasonic transducer 1'.

The ultrasonic transducers 1, 1' of the first and second embodiments are used as a driving source of a handheld ultrasonic device such as an ultrasonic cutter or an ultrasonic dental scaler. As shown in FIGS. 1 and 2, and 17 and 18, the ultrasonic transducers 1, 1' are formed into a columnar shape having, for example, a total length of 21.9 mm and a maximum outer diameter of 4.0 mm, and mainly include: a plurality of piezoelectric elements 8, 9, 10, 11; a front plate 2 and back plate 3 which function as a pair of clamping members for clamping the piezoelectric elements 8, 9, 10, 11; and a side plate 12 which functions as a cover member.

The piezoelectric elements 8, 9, 10, 11 are integrally sintered together with electrodes (silver electrodes) 14, 15, 16, 17, 18 in which silver palladium and the like are used as materials, conductor patterns 23, 25, and an insulating layer 24, to constitute a piezoelectric element unit 28.

Each of the piezoelectric elements 8, 9, 10, 11 is formed into, for example, a rectangular planer shape of 2.5 mm square or a disk-like shape of a diameter of 2.5 mm with using a piezoelectric ceramics material such as PZT (lead zirconate titanate) or barium titanate. Each of the piezoelectric elements 8, 9, 10, 11 is polarized in the thickness direction, and has a positive or negative electrode on the surface or the rear face.

In the piezoelectric element unit 28, the piezoelectric elements 8, 9, 10, 11 and the electrodes 14, 15, 16, 17, 18, and the conductor patterns 23, 25 and the insulating layer 24 are integrally sintered in a state where they are stacked together, so that the piezoelectric elements 8, 9, 10, 11 are electrically connected in parallel. The insulating layer 24 is configured by a resin material which is electrically insulative, ceramic, or the like, and disposed in order to prevent the conductor pattern 25 for the positive side and the front plate 2 from being short-circuited, and avoid situations such as where the side of the piezoelectric elements 8, 9, 10, 11 locally presses that of the front plate 2 (i.e., effectively transmit ultrasonic vibration generated by the piezoelectric elements 8, 9, 10, 11 toward the front plate 2).

In the ultrasonic transducers 1, 1', as shown in FIGS. 1 and 2, and 17 and 18, a positive lead wire 19 and negative lead wire 20 which are configured respectively by covered wires are disposed. The positive lead wire 19 is drawn out to the outside of the back plate 3 from the side of the piezoelectric elements 8, 9, 10, 11 while being passed through a through hole 3c formed in the back plate 3. By contrast, the negative lead wire 20 is fixed in a state where the wire is pressingly contacted with the surface (external face) of the back plate 3 through a lead fixing device 21, in order to ground the transducer body.

Specifically, the electrodes 15, 17 which function as a positive electrode are connected to the positive lead wire 19 through the conductor pattern 25. By contrast, the electrodes 14, 16, 18 which function as a negative electrode are connected to the negative lead wire 20 through the conductor pattern 23 and the body of the back plate 3. Furthermore, the peripheral face (sidewall face) of the piezoelectric element unit 28 which is electrically connected to the lead wires 19, 20 is covered by an insulating layer 22. The insulating layer 22 is configured by, for example, a tape or resin ring in which an insulative polyimide film is used as a material, and ensures the electrical insulation property of the piezoelectric element unit 28 with respect to the inner wall face of the side plate 12. Alternatively, the insulating layer 22 may be formed by applying a liquid insulating material such as an insulating paste to the peripheral face of the piezoelectric element unit 28, or by applying an insulating coat to the inner wall face of the cylindrical side plate 12.

Next, the configurations of the front plate 2, the back plate 3, and the side plate 12, and the structure of joining these members will be described.

As shown in FIGS. 1 and 2, and 17 and 18, the front plate 2 is configured as a metal block in which a titanium alloy or the like is used as a material, and which has a substantially truncated conical shape having a step where the basal end side (the piezoelectric element side) has a smaller diameter. The front plate 2 has an axial length of, for example, $(1/4)\lambda$ with respect to the resonance frequency $\lambda$ of the bodies of the ultrasonic transducers 1, 1', functions as a horn which transmits ultrasonic vibration produced on the side of the piezoelectric element unit 28, and has the forwardmost face which serves as a vibration radiating surface 7. By contrast, the back plate 3 is configured as a metal block in which a titanium alloy or the like is used as a constituting material, and which has a substantially columnar shape having a step where the forward end side (the piezoelectric element side) has a smaller diameter. The above-described lead wires 19, 20 are drawn out from the most basal end face of the back plate 3.

As shown in FIGS. 1 and 2, and 17 and 18, the side plate 12 is formed into a tubular shape (cylindrical shape) with using the above-mentioned titanium alloy as a material. In the first embodiment, the side plate 12 is crimped to each of the front plate 2 and the back plate 3, in a state where the side plate cooperates with the front plate 2 and the back plate 3 to surround the piezoelectric elements 8, 9, 10, 11. More specifically, while the side plate 12 surrounds the piezoelectric elements 8, 9, 10, 11 in a state where the side plate is interposed between the front plate 2 and the back plate 3, the side plate 12 is crimped to the front plate 2 and the back plate 3 through crimp rings 5, 6. The crimp rings 5, 6 which are annular engaging members are configured by using a material such as duralumine. In the second embodiment, the side plate 12 is welded to the front plate 2 and the back plate 3 while surrounding the piezoelectric elements 8, 9, 10, 11 in a state where the side plate is interposed between the front plate 2 and the back plate 3.

In the first and second embodiments, the front plate 2 and the back plate 3 have insertion portions 2a, 3a which are inserted from one and other opening portions 12a, 12b of the cylindrical side plate 12 to clamp the piezoelectric elements 8, 9, 10, 11 (the piezoelectric element unit 28) that are placed inside the cylindrical side plate 12, respectively. Outer diameter portions of the insertion portions 2a, 3a, and an inner diameter portion of the cylindrical side plate 12 are formed so as to have dimensions so that the outer and inner diameter portions are fitted to each other. In the insertion portion 2a of the front plate 2, a counterbore portion 2c in which the most basal end face is slightly recessed is disposed. The piezoelectric element unit 28 is clamped between the bottom face of the counterbore portion 2c disposed in the insertion portion 2a of the front plate 2, and the forwardmost face of the insertion portion 3a of the back plate 3.

In the first embodiment, peripheral edge portions of the opening portions 12a, 12b which are opened in the both ends of the side plate 12 are configured by thinned portions 12c, 12d that are to be fitted (inserted) to the crimp rings 5, 6, respectively. As shown in FIGS. 1 and 2, namely, the thinned portions 12c, 12d of the side plate 12 are crimped to root portions 2b, 3b of the front plate 2 and the back plate 3 (the smaller-diameter portions of the step portions of the front plate 2 and the back plate 3) through the crimp rings 5, 6, in a state where (outer diameter portions) of the thinned portions 12c, 12d of the side plate 12 are inserted into the insides of the crimp rings 5, 6, and the insertion portions 2a, 3a are inserted into the opening portions 12a, 12b of the side plate 12, respectively.

The axial length of the side plate 12 is set so that a small clearance is formed between the step faces (the step faces which are parallel to the vibration radiating surface 7 or the most basal end face of the back plate 3) of the root sides of the insertion portions 2a, 3a of the front plate 2 and the back plate 3, and the both ends of the cylindrical side plate 12, in a state where the side plate 12 is interposed between the front plate 2 and back plate 3 which clamp the piezoelectric element unit 28. As shown in FIG. 3, namely, the side plate 12 is crimped to each of the front plate 2 and the back plate 3 in a state where the piezoelectric elements 8, 9, 10, 11 (the piezoelectric element unit 28) are pressed through the front plate 2 and the back plate 3. According to the configuration, the property of transmitting vibration from the piezoelectric elements 8, 9, 10, 11 toward the front plate 2 can be improved.

In the second embodiment, as shown in FIGS. 17 and 18, peripheral edge portions 12e, 12f (mainly, the end faces of the peripheral edges of the opening portions 12a, 12b) of the opening portions 12a, 12b of the side plate 12 are welded to the step portions 2d, 3d (mainly, the step faces which are parallel to the vibration radiating surface 7 or the most basal end face of the back plate 3) of the front plate 2 and the back plate 3, respectively, in a state where the insertion portions 2a, 3a are inserted from the opening portions 12a, 12b of the side plate 12 and the piezoelectric element unit 28 are clamped.

The axial length of the side plate 12 is set so that a small clearance is formed between the step portions 2d, 3d (the step faces) of the front plate 2 and the back plate 3, and the both ends of the cylindrical side plate 12, in a state where the side plate 12 is interposed between the front plate 2 and the back plate 3 while clamping the piezoelectric element unit 28. As shown in FIG. 19, namely, the side plate 12 is welded to the front plate 2 and the back plate 3 in a state where the piezoelectric elements 8, 9, 10, 11 (the piezoelectric element unit 28) are pressed through the front plate 2 and the back plate 3. According to the configuration, the property of transmitting vibration from the piezoelectric elements 8, 9, 10, 11 toward the front plate 2 can be improved.

Next, a method of producing the ultrasonic transducer 1 of the first embodiment will be described with reference mainly to FIGS. 2 and 3.

As shown in FIG. 2, in a state where the piezoelectric elements 8, 9, 10, 11, the electrodes 14, 15, 16, 17, 18, the conductor patterns 23, 25, and the insulating layer 24 are stacked so that the piezoelectric elements 8, 9, 10, 11 are connected electrically in parallel, first, they are subjected to a sintering process to integrally sinter the piezoelectric element unit 28. Then, the peripheral face (sidewall face) of the piezoelectric element unit 28 is covered by the insulating layer 22, and the lead wires 19, 20 are laid.

As shown in FIGS. 2 and 3, while the front plate 2 and the back plate 3 are placed at positions where the piezoelectric element unit 28 (the piezoelectric elements 8, 9, 10, 11) is clamped from the both sides, the side plate 12 is then placed at a position where the side plate cooperates with the front plate 2 and the back plate 3 to surround the piezoelectric element unit 28. More specifically, while the side plate 12 in which the crimp rings 5, 6 are attached to the thinned portions 12c, 12d is placed at a position where it surrounds the piezoelectric element unit 28 (the piezoelectric elements 8, 9, 10, 11), the front plate 2 and the back plate 3 are placed (the insertion portions 2a, 3a are inserted into the opening portions 12a, 12b of the side plate 12) at positions where the side plate 12 and the piezoelectric element unit 28 are clamped from the both sides. As shown in FIG. 3, in a state where the piezoelectric element unit 28 is pressed by an adequate load in directions of P1, P2 through the front plate 2 and back plate 3 which are placed in this way, furthermore, the peripheries of the crimp rings 5, 6 are inwardly pressed to perform a crimping process. In this case, the thinned portions 12c, 12d in the both ends of the side plate 12 are plastically deformed in a diameter-reducing direction together with the crimp rings 5, 6, whereby the front plate 2 and the back plate 3 (the root portions 2b, 3b of the insertion portions 2a, 3a), and the side plate 12 (the thinned portions 12c, 12d) are integrally coupled to each other. After the above-described crimping step, it is possible to obtain the ultrasonic transducer 1 shown in FIG. 1.

As described above, according to the ultrasonic transducer 1 of the first embodiment and the method of producing it, the piezoelectric elements 8, 9, 10, 11 (the piezoelectric element unit 28) can be installed as internal components without using a thread structure, by crimping the side plate 12 between the front plate 2 and back plate 3 which clamp the piezoelectric elements 8, 9, 10, 11, and hence it is possible to eliminate the necessity of ensuring a region for forming the thread structure in the product body (the body of the ultrasonic transducer 1), and the like. Consequently, the degree of freedom in selection of the sizes of the piezoelectric elements and the product body is enhanced, and hence it is possible to realize miniaturization of the ultrasonic transducer, increase of the output power of the ultrasonic transducer due to employment of piezoelectric elements having a relatively large size, etc. In the first embodiment, moreover, a thread structure is not required as described above, and therefore the component cost can be reduced.

According to the ultrasonic transducer 1 of the first embodiment and the method of producing it, moreover, individual members are joined together by crimping without using a thread structure as described above. When crimping is performed while applying, for example, an adequate load from the both sides of the front plate 2 and the back plate 3, therefore, the piezoelectric elements 8, 9, 10, 11 (the piezoelectric element unit 28) can be installed between the front plate 2 and the back plate 3 by an adequate holding (clamping) force without applying torsional stress to the piezoelectric elements. Therefore, the piezoelectric elements can be installed by an adequate holding force while suppressing positional deviation during installation of the piezoelectric elements, and hence the vibration characteristics of the ultrasonic transducer can be prevented from being dispersed. Moreover, breakage of the piezoelectric elements and the like caused by mechanical stress can be prevented from occurring. In the first embodiment, in the case of joining the members, to-be-joined portions are not required to be heated and melted at a high temperature unlike the case where, for example, welding is used. Therefore, the degree of freedom in selection of the materials of the front plate 2, the back plate 3, and the side plate 12 can be enhanced (also a material having a high melting point can be easily selected), and welding apparatuses which are relatively expensive are not required to be installed. Consequently, it is possible to improve the productivity of the ultrasonic transducer.

Next, a method of producing the ultrasonic transducer 1' of the second embodiment will be described with reference mainly to FIGS. 18 and 19.

As shown in FIG. 18, in a state where the piezoelectric elements 8, 9, 10, 11, the electrodes 14, 15, 16, 17, 18, the conductor patterns 23, 25, and the insulating layer 24 are stacked so that the piezoelectric elements 8, 9, 10, 11 are connected electrically in parallel, first, they are subjected to a sintering process to integrally sinter the piezoelectric element unit 28. Then, the peripheral face (sidewall face) of the piezoelectric element unit 28 is covered by the insulating layer 22, and the lead wires 19, 20 are laid.

As shown in FIGS. 18 and 19, while the side plate 12 is placed at a position where it surrounds the piezoelectric element unit 28 (the piezoelectric elements 8, 9, 10, 11), the front plate 2 and the back plate 3 are placed (the insertion portions 2a, 3a are inserted into the opening portions 12a, 12b of the side plate 12) at positions where the side plate 12 and the piezoelectric element unit 28 are clamped from the both sides. As shown in FIG. 19, in a state where the piezoelectric element unit 28 is pressed by an adequate load in directions of P1, P2 through the front plate 2 and back plate 3 which are placed in this way, furthermore, the front plate 2, the back plate 3, and the side plate 12 are welded together (welded portions 5a, 6a are formed).

Specifically, as shown in FIG. 19, a laser illuminating device 29 is used, and the peripheral edge portions 12e, 12f of the opening portions 12a, 12b of the side plate 12, and the step portions 2d, 3d of the front plate 2 and the back plate 3 are laser welded together while the laser illuminating device 29 is revolved around the both ends of the side plate 12. In the laser welding, steps such as that of setting current supplying electrodes on the to-be-welded members (the front plate 2, the back plate 3, and the side plate 12) are not required, and hence setting for welding is facilitated. In place of such laser welding, electron beam welding may be used in which electrons generated by heating a filament in a vacuum are accelerated by a high voltage, and the accelerated electrons are supplied to to-be-welded portions while the electrons are focused by an electromagnetic coil or the like. After the welding step due to such electron beam welding or the above-described laser welding, it is possible to obtain the ultrasonic transducer 1' shown in FIG. 17.

As described above, according to the ultrasonic transducer 1' of the second embodiment and the method of producing it, the front plate 2 and back plate 3 which clamp the piezoelectric elements 8, 9, 10, 11 (the piezoelectric element unit 28) are welded together through the side plate 12 without using a thread structure, and hence it is possible to eliminate the necessity of ensuring a region for forming the thread structure in the product body (the body of the ultrasonic transducer 1), and the like. Consequently, the degree of freedom in selection of the sizes of the piezoelectric elements and the product body is enhanced, and hence it is possible to realize miniaturization of the ultrasonic transducer, increase of the output power of the ultrasonic transducer due to employment of piezoelectric elements having a relatively large size, etc. In the second embodiment, moreover, a thread structure is not required as described above, and therefore the component cost can be reduced. Since a welding process in which a mechanical load is hardly applied is employed in the joining of the individual members, a material which is relatively low in hardness can be selected as a material constituting the front plate 2 and the back plate 3.

According to the ultrasonic transducer 1' of the second embodiment and the method of producing it, without using a thread structure and the like as described above, welding is used in the joining of the front plate 2 and the back plate 3 (and the side plate 12), and performed while applying an appropriate load from the both side of the front plate 2 and the back plate 3. Therefore, torsional stress or the like is not applied to the piezoelectric elements 8, 9, 10, 11 (the piezoelectric element unit 28). Moreover, the piezoelectric elements can be installed by an adequate holding (clamping) force between the front plate 2 and the back plate 3. Therefore, the piezoelectric elements can be installed by an adequate holding force while suppressing positional deviation during installation of the piezoelectric elements, and hence the vibration characteristics of the ultrasonic transducer 1' can be prevented from being dispersed. Moreover, breakage of the piezoelectric elements and the like caused by mechanical stress can be prevented from occurring.

Third Embodiment

Figure 4:
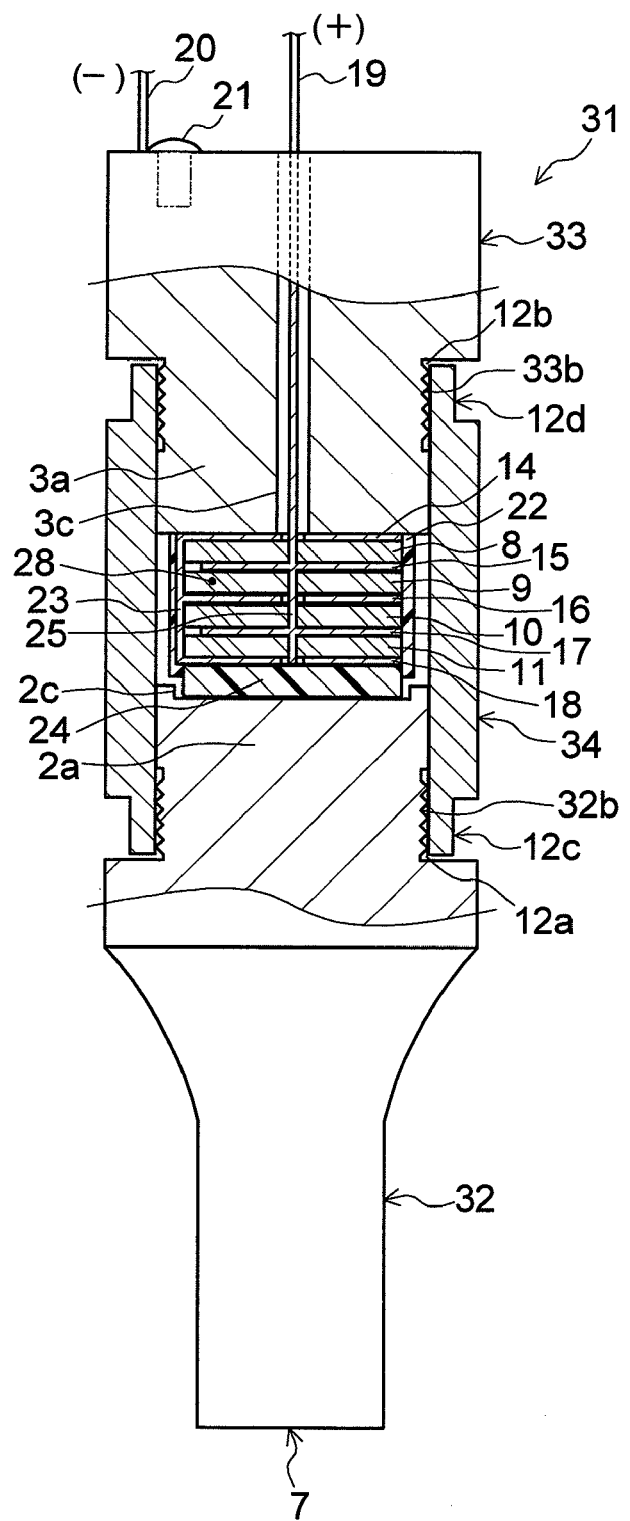
FIG. 4 is a front view showing in partially section an ultrasonic transducer of a third embodiment of the invention.

Next, a third embodiment of the invention will be described with reference to FIG. 4. FIG. 4 is a front view showing in partially section an ultrasonic transducer 31 of the embodiment. In FIG. 4, components which are identical with those of the ultrasonic transducer 1 of the first embodiment shown in FIGS. 1 to 3 are denoted by the same reference numerals, and their description is omitted.

As shown in FIG. 4, the ultrasonic transducer 31 of the embodiment includes a front plate 32, a back plate 33, and a side plate 34 in place of the front plate 2, back plate 3, and side plate 12 which are disposed in the ultrasonic transducer 1 of the first embodiment, and each of the front plate 32 and the back plate 33 is crimped to the side plate 34 without using a crimp ring. Namely, a metal material which is relatively soft so as to be easily plastically deformed in a crimping process, such as duralumine or soft iron is used as a material constituting the front plate 32, the back plate 33, and the side plate 34.

In order to allow the side plate 34 to easily bite the front plate 32 and the back plate 33 in a crimping process, as shown in FIG. 4, asperities are formed in the surfaces (to-be-crimped portions) of root portions 32b, 33b of the insertion portions 2a, 3a of the front plate 32 and the back plate 33. Alternatively, such asperities to be formed in to-be-crimped portions may be disposed on the side (of the inner wall faces of the thinned portions 12c, 12d) of the side plate 34, or disposed in both the front plate 32 and the back plate 33, and the side plate 34.

In the ultrasonic transducer 31 of the embodiment, in a state where the piezoelectric element unit 28 is pressed by an adequate load through the front plate 32 and back plate 33 which are configured as described above, the peripheries of the thinned portions 12c, 12d at the both ends of the side plate 34 are inwardly pressed to perform a crimping process, whereby the inner wall side materials of the thinned portions 12c, 12d bite the asperities in the surfaces of the root portions 32b, 33b of the insertion portions 2a, 3a of the front plate 32 and the back plate 33, so that the front plate 32 and the back plate 33 are integrally joined with the side plate 34.

According to the ultrasonic transducer 31 of the embodiment and the method of producing it, therefore, application of torsional stress to the piezoelectric elements 8, 9, 10, 11 can be suppressed, the vibration characteristics can be prevented from being dispersed, and miniaturization and increase of the output power are enabled while improving the productivity. In the embodiment, particularly, the crimp rings which are used in the first embodiment are not necessary, and hence the production cost can be reduced.

Fourth Embodiment

Figure 5:
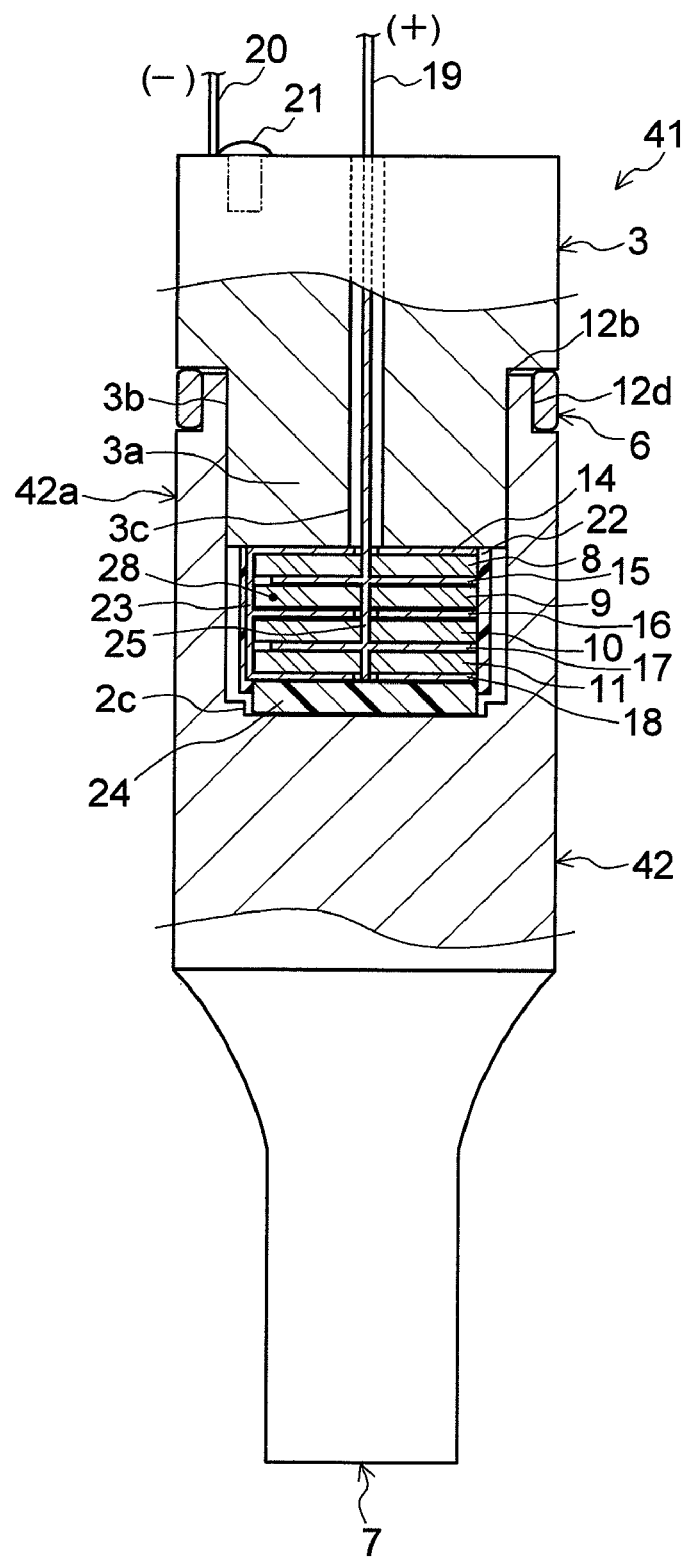
FIG. 5 is a front view showing in partially section an ultrasonic transducer of a fourth embodiment of the invention.

Next, a fourth embodiment of the invention will be described with reference to FIG. 5. FIG. 5 is a front view showing in partially section an ultrasonic transducer 41 of the embodiment. In FIG. 5, components which are identical with those of the ultrasonic transducer 1 of the first embodiment shown in FIGS. 1 to 3 are denoted by the same reference numerals, and their description is omitted.

In the ultrasonic transducer 41 of the embodiment, as shown in FIG. 5, the crimp ring 5 which is disposed in the ultrasonic transducer 1 of the first embodiment is omitted, and a front plate 42 having a cover portion 42a is provided in place of the front plate 2 and the side plate 12. Namely, the front plate 42 is realized by configuring the front plate 2 and the side plate 12 in the first embodiment by a single member.

In the ultrasonic transducer 41, in a state where the piezoelectric element unit 28 is pressed by an adequate load through the front plate 42 and the back plate 3, the periphery of the crimp ring 6 is inwardly pressed to perform a crimping process, whereby the thinned portion 12d of the cover portion 42a of the front plate 42 is plastically deformed in a radial direction together with the crimp ring 6, so that the cover portion 42a (a constituting portion of the side plate 12 in the first embodiment) of the front plate 42 and the back plate 3 (the root portion 3b of the insertion portion 3a) are joined to each other.

FIG. 5 exemplarily shows the configuration where the front plate 42 and the back plate 3 are crimped to each other through the crimp ring 6. Alternatively, the front plate 42 and the back plate 3 may be configured by a metal material which is relatively soft, such as duralumine, and asperities may be formed in the inner wall of the thinned portion 12d disposed in the cover portion 42a of the front plate 42, and the surface of the root portion 3b disposed in the insertion portion 3a of the back plate 3, whereby the crimp ring 6 is omitted and the front plate 42 and the back plate 3 are crimped to each other.

According to the ultrasonic transducer 41 of the embodiment, in addition to the effects of the first or third embodiment, places where crimping is to be performed, and the number of components are reduced. Therefore, the component cost can be reduced, and the production efficiency can be improved.

Fifth Embodiment

Figure 6:
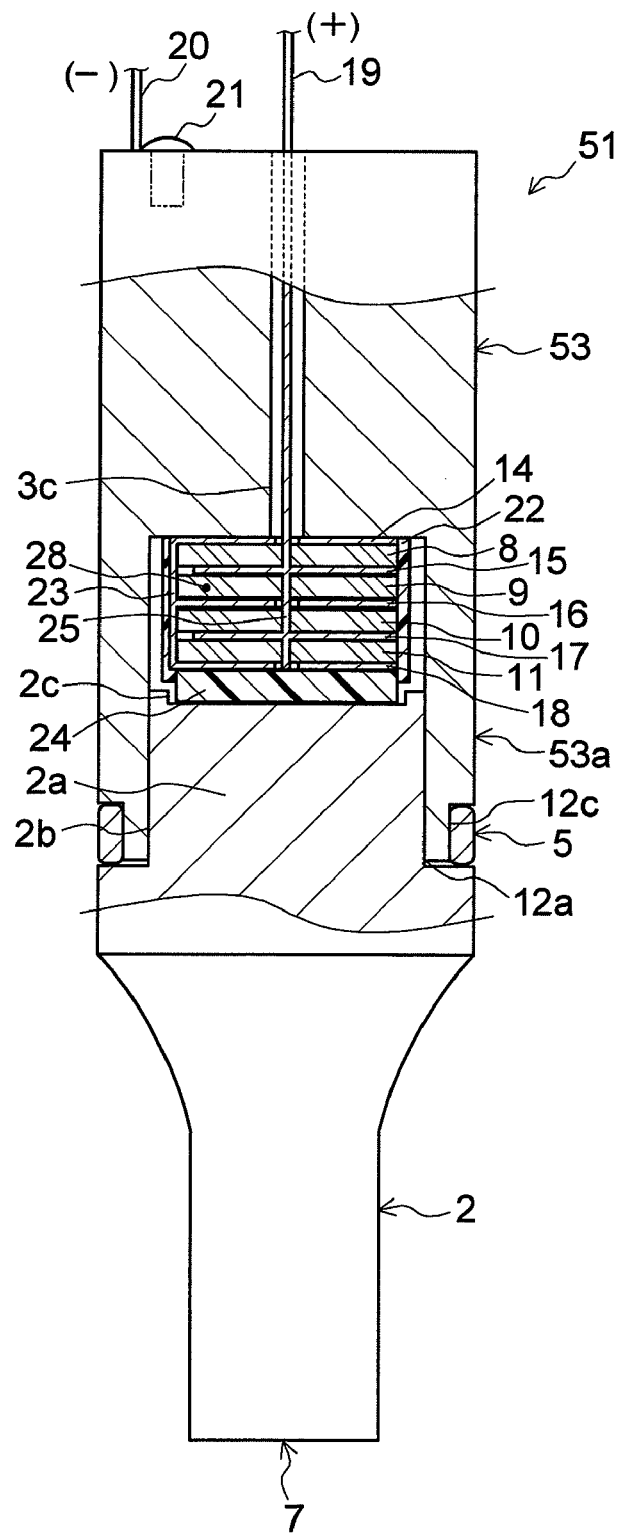
FIG. 6 is a front view showing in partially section an ultrasonic transducer of a fifth embodiment of the invention.

Next, a fifth embodiment of the invention will be described with reference to FIG. 6. FIG. 6 is a front view showing in partially section an ultrasonic transducer 51 of the embodiment. In FIG. 6, components which are identical with those of the ultrasonic transducer 1 of the first embodiment shown in FIGS. 1 to 3 are denoted by the same reference numerals, and their description is omitted.

As shown in FIG. 6, the ultrasonic transducer 51 of the embodiment includes a back plate 53 having a cover portion 53a in place of the back plate 3 and side plate 12 which are disposed in the ultrasonic transducer 1 of the first embodiment. Namely, the back plate 53 is realized by configuring the back plate 3 and the side plate 12 in the first embodiment by a single member.

In the ultrasonic transducer 51, in a state where the piezoelectric element unit 28 is pressed by an adequate load through the front plate 2 and the back plate 53, the periphery of the crimp ring 5 is inwardly pressed to perform a crimping process, whereby the thinned portion 12c of the cover portion 53a of the back plate 53 is plastically deformed in a radial direction together with the crimp ring 5, so that the cover portion 53a (a constituting portion of the side plate 12 in the first embodiment) of the back plate 53 and (the root portion 2b of the insertion portion 2a of) the front plate 2 are joined to each other.

FIG. 6 exemplarily shows the configuration where the front plate 2 and the back plate 53 are crimped to each other through the crimp ring 5. Alternatively, the front plate 2 and the back plate 53 may be configured by a metal material which is relatively soft, such as duralumine, and asperities may be formed in the inner wall of the thinned portion 12c disposed in the cover portion 53a of the back plate 53, and the surface of the root portion 2b disposed in the insertion portion 2a of the front plate 2, whereby the crimp ring 5 is omitted and the front plate 2 and the back plate 53 are crimped to each other.

According to the ultrasonic transducer 51 of the embodiment, as in the effects of the fourth embodiment, places where crimping is to be performed, and the number of components are reduced. Therefore, the component cost can be reduced, and the production efficiency can be improved.

Sixth Embodiment

Figure 20:
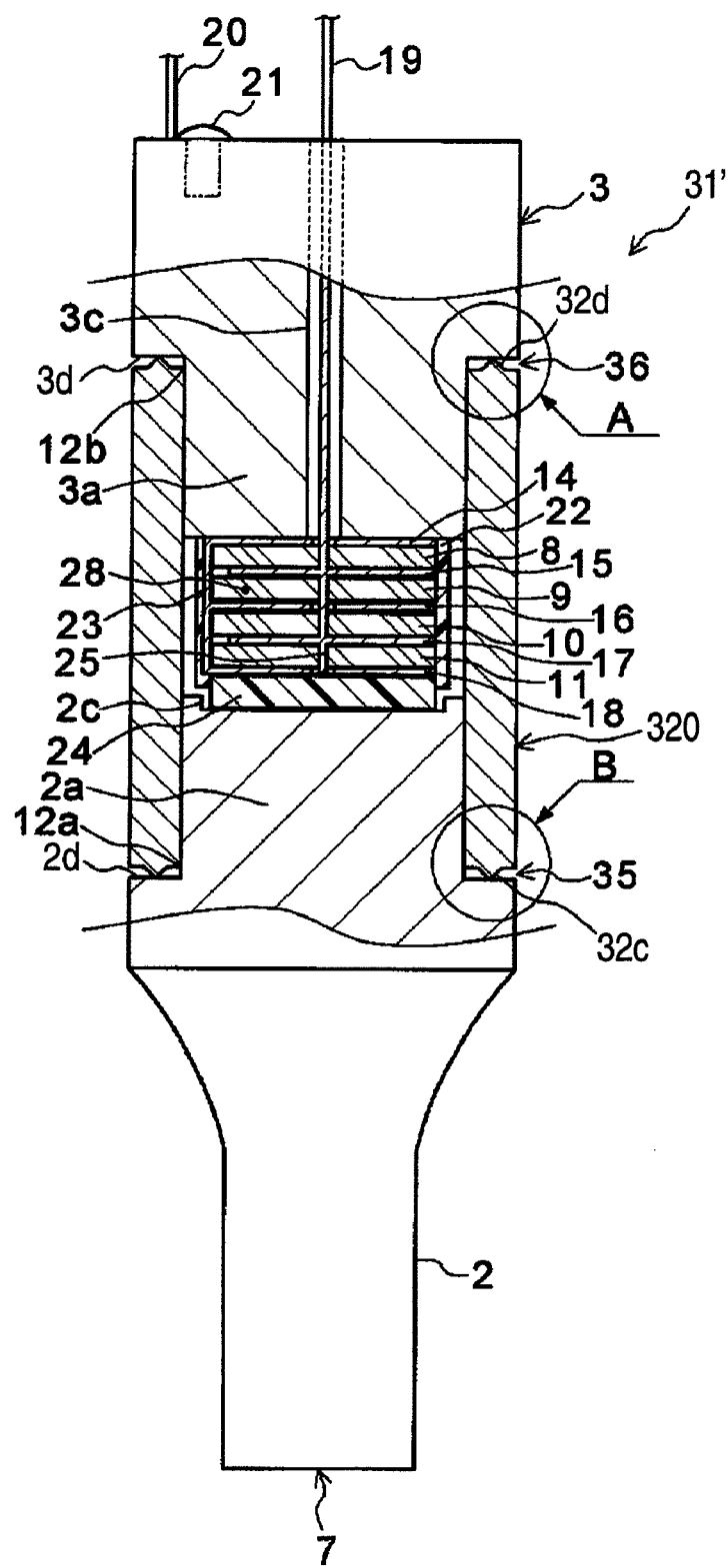
FIG. 20 is a front view showing in partially section an ultrasonic transducer of a sixth embodiment of the invention.
Figure 21:
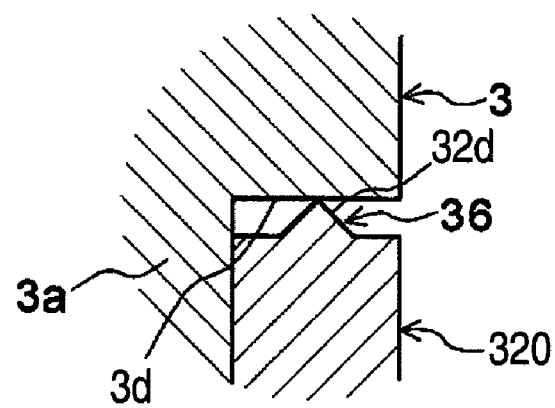
FIG. 21 is a detail view of a portion A in the ultrasonic transducer shown in FIG. 20.
Figure 22:
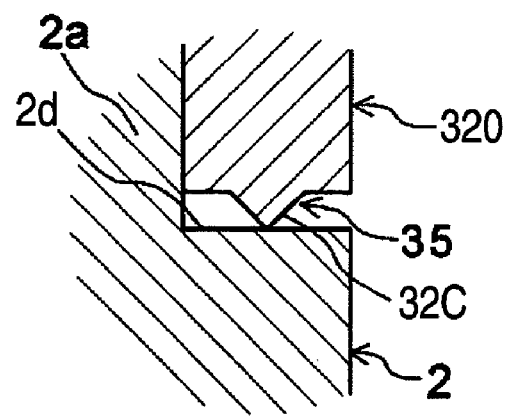
FIG. 22 is a detail view of a portion B in the ultrasonic transducer shown in FIG. 20.

Next, a sixth embodiment of the invention will be described with reference to FIGS. 20 to 22. FIG. 20 is a front view showing in partially section an ultrasonic transducer 31' of the embodiment, FIG. 21 is a detail view of a portion A in the ultrasonic transducer 31' shown in FIG. 20, and FIG. 22 is a detail view of a portion B in the ultrasonic transducer 31' shown in FIG. 20. In FIGS. 20 to 22, components which are identical with those of the ultrasonic transducer 1' of the second embodiment shown in FIGS. 17 to 19 are denoted by the same reference numerals, and their description is omitted.

As shown in FIG. 20, the ultrasonic transducer 31' of the embodiment includes a side plate 320 in place of the side plate 12 disposed in the ultrasonic transducer 1' in the second embodiment. In the ultrasonic transducer 31', in a state where the piezoelectric element unit 28 is pressed by an adequate load through the front plate 2 and back plate 3, the above-mentioned side plate 320 is welded to the front plate 2 and the back plate 3 by using spot welding which is an electric welding process.

As shown in FIGS. 20 to 22, in order to enable the current supply to be well performed in spot welding, rib-like projections 32c, 32d are formed in to-be-welded portions 35, 36 which are between the front plate 2 and the back plate 3, and the side plate 320. The rib-like projections 32c, 32d are formed on the end faces of the peripheries of the opening portions 12a, 12b of the side plate 320. More specifically, the projections 32c, 32d are projected from the both end sides of the side plate 320 toward the step portions 2d, 3d (the step faces which are parallel to the vibration radiating surface 7 or the most basal end face of the back plate 3) of the front plate 2 and the back plate 3, and formed so as to circulate along the peripheral edges of the opening portions 12a, 12b, respectively.

The axial length of the side plate 320 is configured (adjusted) so that, in a state where the side plate 320 is interposed between the front plate 2 and the back plate 3 while clamping the piezoelectric element unit 28, a pressing force required in the spot welding can be applied to the to-be-welded portions 35, 36 which are between the step portions 2d, 3d (the step faces) of the front plate 2 and the back plate 3, and the projections 32c, 32d at the both ends of the side plate 320.

FIG. 20 exemplarily shows the configuration where the rib-like projections 32c, 32d are disposed on the side of the side plate 320. Alternatively, the rib-like projections may be disposed on the sides of the front plate 2 and the back plate 3. For example, the side plate 12 in the second embodiment in which projections are not formed is used, and rib-like projections which are projected from the side of the step portions 2d, 3d (the above-mentioned step faces) of the front plate 2 and the back plate 3, toward the both ends of the side plate 320 may be disposed in the front plate 2 and the back plate 3.

As described above, according to the ultrasonic transducer 31' of the embodiment and the method of producing it, generation of torsional stress and the like that may be applied to the piezoelectric elements during installation can be suppressed, dispersion of the vibration characteristics can be suppressed. Moreover, miniaturization of the ultrasonic transducer body, and increase of the output power are enabled. In the embodiment, because of the configurations such as that where the rib-like projections are formed in the to-be-welded portions which are between the front plate and the back plate, and the side plate, it is possible to employ spot welding in which a welding process is usually enabled by supplying a current for a very short time period of from several milliseconds to several hundred milliseconds.

Therefore, the efficiency of welding process can be improved. In the embodiment, in a step of, in welding, pressing the piezoelectric element unit 28 through the front plate 2 and the back plate 3, furthermore, a pressing force required in the spot welding can be applied simultaneously to the to-be-welded portions in which the projections are formed. Therefore, the to-be-welded portions can be efficiently welded.

Seventh Embodiment

Figure 23:
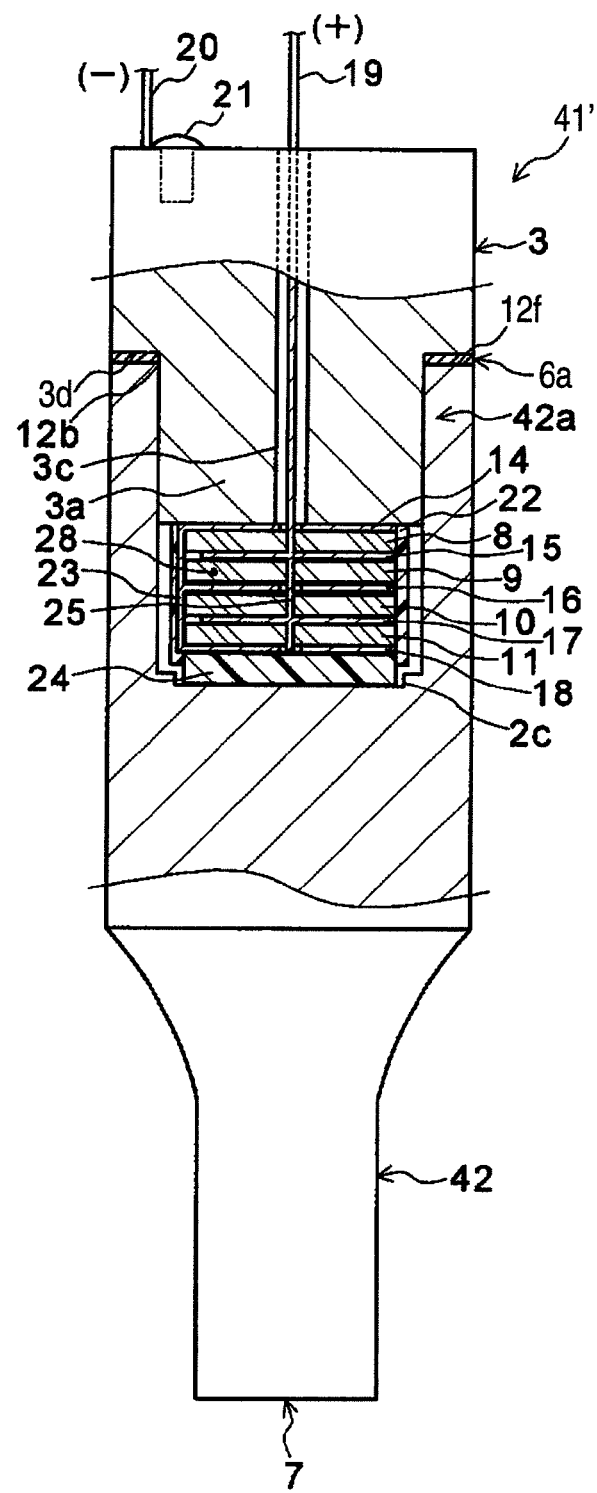
FIG. 23 is a front view showing in partially section an ultrasonic transducer of a seventh embodiment of the invention.

Next, a seventh embodiment of the invention will be described with reference to FIG. 23. FIG. 23 is a front view showing in partially section an ultrasonic transducer 41' of the embodiment. In FIG. 23, components which are identical with those of the ultrasonic transducer 1' of the second embodiment shown in FIGS. 17 to 19 are denoted by the same reference numerals, and their description is omitted.

As shown in FIG. 23, the ultrasonic transducer 41' of the embodiment includes a front plate 42 having a cover portion 42a in place of the front plate 2 and side plate 12 which are disposed in the ultrasonic transducer 1' of the second embodiment. Namely, the front plate 42 is realized by configuring the front plate 2 and the side plate 12 in the second embodiment by a single member.

In the ultrasonic transducer 41', in a state where the piezoelectric element unit 28 is pressed by an adequate load through the front plate 42 and the back plate 3, the cover portion 42a (a constituting portion of the side plate 12 in the second embodiment) of the front plate 42 and the back plate 3 are welded to each other by using laser welding or electron beam welding. Specifically, the peripheral edge portion 12f of the opening portion 12b of the cover portion 42a, and the step portion 3d (step face) of the back plate 3 are welded to each other (the welded portion 6a is formed between them).

FIG. 23 exemplarily shows the configuration where the welded portion 6a is formed by laser welding or electron beam welding. Alternatively, a rib-like projection may be disposed in the peripheral edge portion 12f (the end face of the periphery of the opening portion 12b) of the opening portions 12b of the cover portion 42a, or the step potion 3d (step face) of the back plate 3, and the front plate 42 and the back plate 3 may be welded to each other by spot welding.

According to the ultrasonic transducer 41' of the embodiment, in addition to the effects of the second or sixth embodiment, places where welding is to be performed, and the number of components are reduced. Therefore, the production cost can be reduced, and the production efficiency can be improved.

Eighth Embodiment

Figure 24:
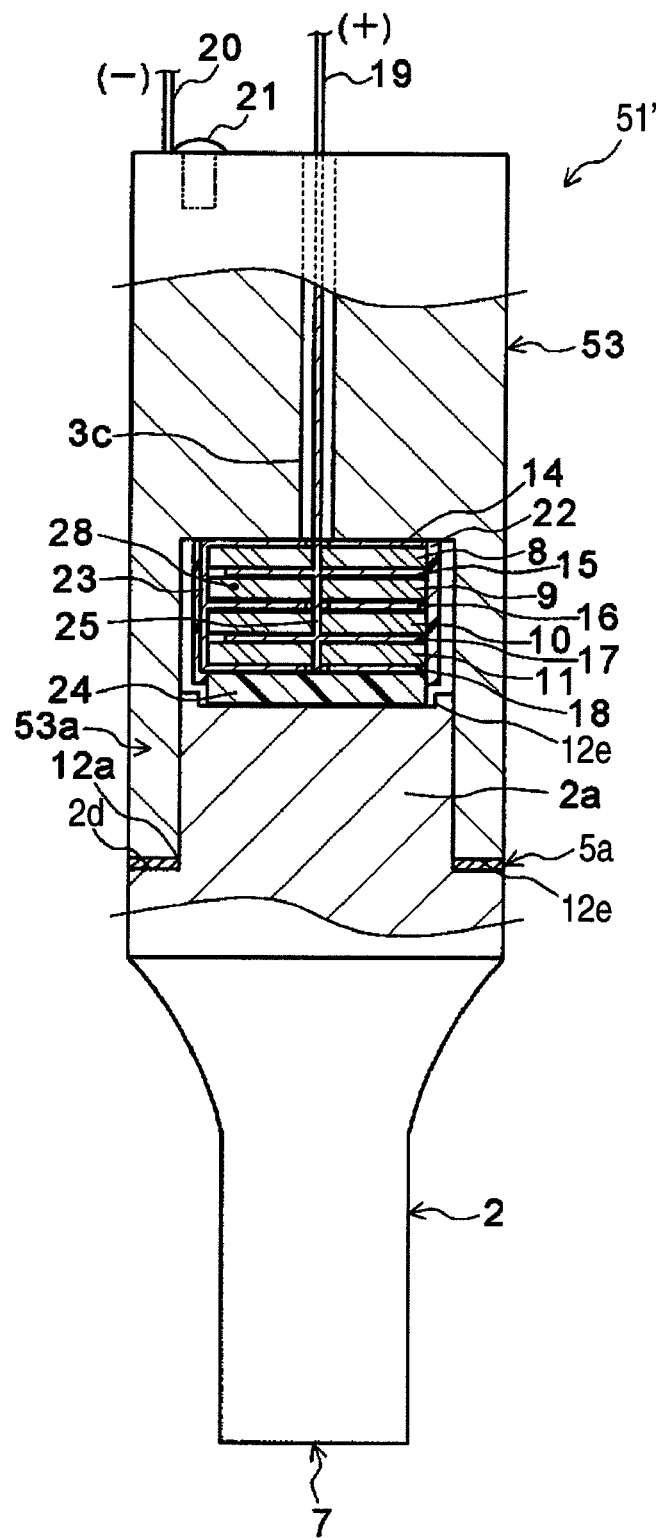
FIG. 24 is a front view showing in partially section an ultrasonic transducer of an eighth embodiment of the invention.

Next, an eighth embodiment of the invention will be described with reference to FIG. 24. FIG. 24 is a front view showing in partially section an ultrasonic transducer 51' of the embodiment. In FIG. 24, components which are identical with those of the ultrasonic transducer 1' of the second embodiment shown in FIGS. 17 to 19 are denoted by the same reference numerals, and their description is omitted.

As shown in FIG. 24, the ultrasonic transducer 51' of the embodiment includes a back plate 53 having a cover portion 53a in place of the back plate 3 and side plate 12 which are disposed in the ultrasonic transducer 1' of the second embodiment. Namely, the back plate 53 is realized by configuring the back plate 3 and the side plate 12 in the second embodiment by a single member.

In the ultrasonic transducer 51', in a state where the piezoelectric element unit 28 is pressed by an adequate load through the front plate 2 and the back plate 53, the cover portion 53a (a constituting portion of the side plate 12 in the second embodiment) of the back plate 53 and the front plate 2 are welded to each other by using laser welding or electron beam welding. Specifically, the peripheral edge portion 12e of the opening portion 12a of the cover portion 53a, and the step portion 2d (step face) of the front plate 2 are welded to each other (the welded portion 5a is formed between them).

FIG. 24 exemplarily shows the configuration where the welded portion 5a is formed by laser welding or electron beam welding. Alternatively, a rib-like projection may be disposed in the peripheral edge portion 12e (the end face of the periphery of the opening portion 12a) of the opening portions 12a of the cover portion 53a, or the step potion 2d (step face) of the front plate 2, and the front plate 2 and the back plate 53 may be welded to each other by spot welding.

According to the ultrasonic transducer 51' of the embodiment, as in the effects of the seventh embodiment, places where welding is to be performed, and the number of components are reduced. Therefore, the production cost can be reduced, and the production efficiency can be improved.

Ninth and Tenth Embodiments

Figure 7:
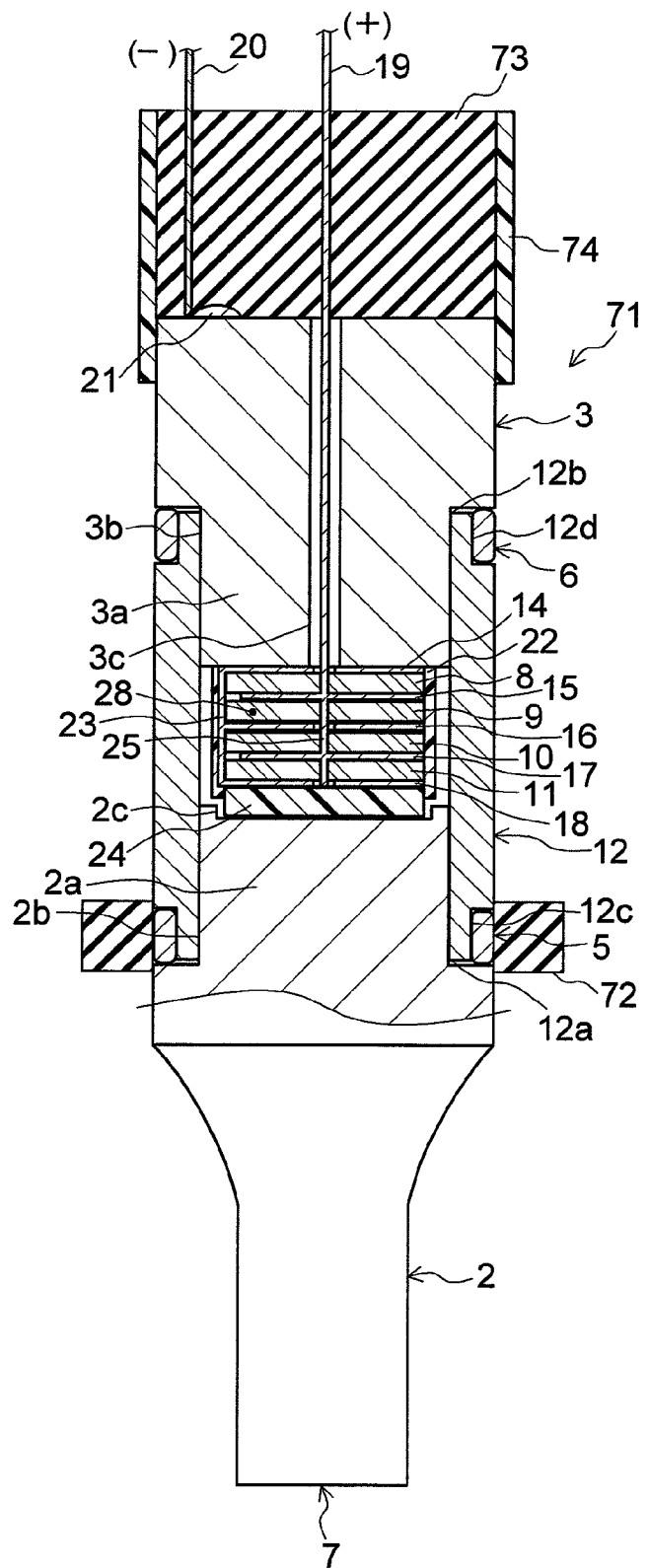
FIG. 7 is a front view showing in partially section an ultrasonic transducer of a ninth embodiment of the invention.
Figure 25:
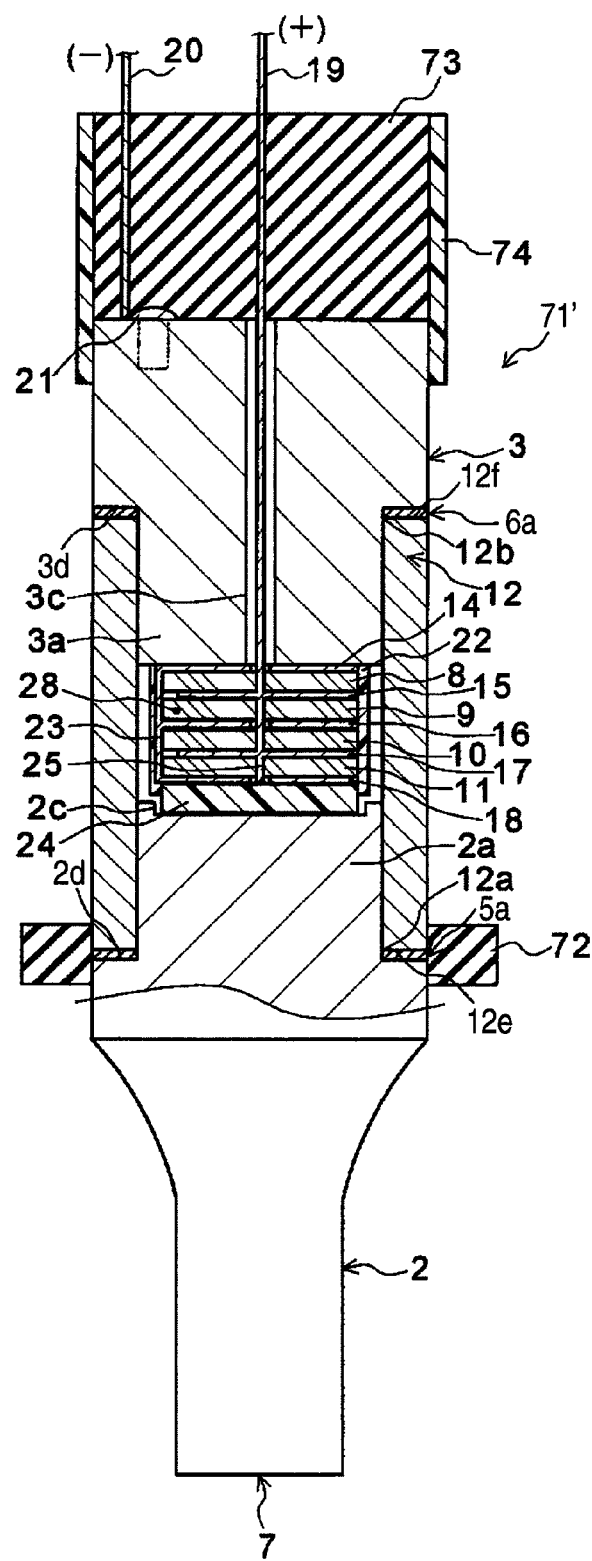
FIG. 25 is a front view showing in partially section an ultrasonic transducer of a tenth embodiment of the invention.

Next, ninth and tenth embodiments of the invention will be described with reference to FIGS. 7 and 25. FIG. 7 is a front view showing in partially section an ultrasonic transducer 71 of the ninth embodiment, and FIG. 25 is a front view showing in partially section an ultrasonic transducer 71' of the tenth embodiment. In FIGS. 7 and 25, components which are identical with those of the ultrasonic transducer 1, 1' of the first and second embodiments shown in FIGS. 1 to 3 and 17 to 19 are denoted by the same reference numerals, and their description is omitted.

The ultrasonic transducer 71 of the ninth embodiment is configured by, in addition to the configuration of the ultrasonic transducer 1 of the first embodiment, including buffer members 72, 73 which function as a damper member for attenuating unwanted vibrations, and a heat shrinkable tube 74. The ultrasonic transducer 71' of the tenth embodiment is configured by, in addition to the configuration of the ultrasonic transducer 1' of the second embodiment, including buffer members 72, 73 which function as a damper member for attenuating unwanted vibration, and a heat shrinkable tube 74. In the ninth and tenth embodiments, the buffer member 72 is formed into, for example, a ring-like shape, and fixed by an adhesive agent or the like to both the peripheral faces of the front plate 2 and the side plate 12. By contrast, the buffer member 73 is formed into, for example, a columnar shape, and fixed to the most basal end face of the back plate 3 by the heat shrinkable tube 74.

The buffer members 72, 73 are disposed in order to eliminate unwanted vibrations (mainly, vibrations outside the band of vibrations generated by the piezoelectric elements 8, 9, 10, 11) which may be produced in the body of the ultrasonic transducer 71. Namely, the buffer members 72, 73 are configured by a material which is at least lower in hardness than the above-described front and back plates 2, 3 made of a titanium alloy. As the material constituting the buffer members 72, 73, specifically, a urethane resin containing lead titanate is for example used. The buffer members 72, 73 having the shape which protrudes from the outer shape of the ultrasonic transducer body perform the function of eliminating unwanted vibrations, and are used also as, in the case where the ultrasonic transducer 71 is attached as a vibration source (inner component) to the inside of a case of an ultrasonic device such as an ultrasonic cutter or an ultrasonic dental scaler, attached portions (convex portions which are to be fitted to recesses disposed in the case of the ultrasonic device).

The heat shrinkable tube 74 which is made of a silicone resin, a fluorine resin, or the like is attached to a basal end portion of the back plate 3, and the interior of the heat shrinkable tube 74 is filled with lead titanate in a powder state and a molten urethane resin, and thereafter a heat treatment is performed, whereby the buffer member 73 is fixed to the most basal end face of the back plate 3.

FIG. 7 exemplarily shows the configuration where the buffer members 72, 73 (and the heat shrinkable tube 74) are attached to the ultrasonic transducer 1 shown in FIGS. 1 to 3. Alternatively, the buffer members 72, 73 may be attached to the ultrasonic transducers 31, 41, 51 shown in FIGS. 4, 5, and 6. The body of the ultrasonic transducer may be configured by removing the heat shrinkable tube 74 from the back plate 3 after the buffer member 73 is fixed.

FIG. 25 exemplarily shows the configuration where the buffer members 72, 73 (and the heat shrinkable tube 74) are attached to the ultrasonic transducer 1'. Alternatively, the buffer members 72, 73 may be attached to the ultrasonic transducers 31', 41', 51' shown in FIGS. 20, 23, and 24. The body of the ultrasonic transducer may be configured by removing the heat shrinkable tube 74 from the back plate 3 after the buffer member 73 is fixed.

As described above, according to the ultrasonic transducers 71, 71' of the ninth and tenth embodiments, in addition to the effects of any one of the above-described embodiments, unwanted vibrations which may be produced in the ultrasonic transducer body can be eliminated, portions to be attached to a case of an ultrasonic device can be configured, and vibrations which may be transmitted to the case of the ultrasonic device (for example, the body of a handheld ultrasonic device) can be attenuated.

Eleventh Embodiment

Figure 8:
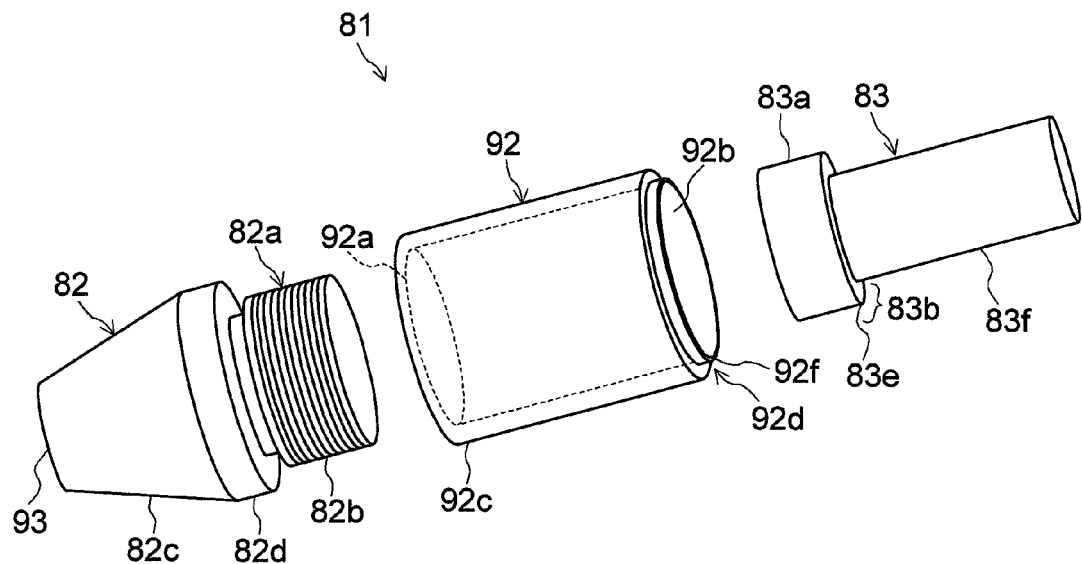
FIG. 8 is an exploded perspective view of an ultrasonic transducer of an eleventh embodiment of the invention.
Figure 10:
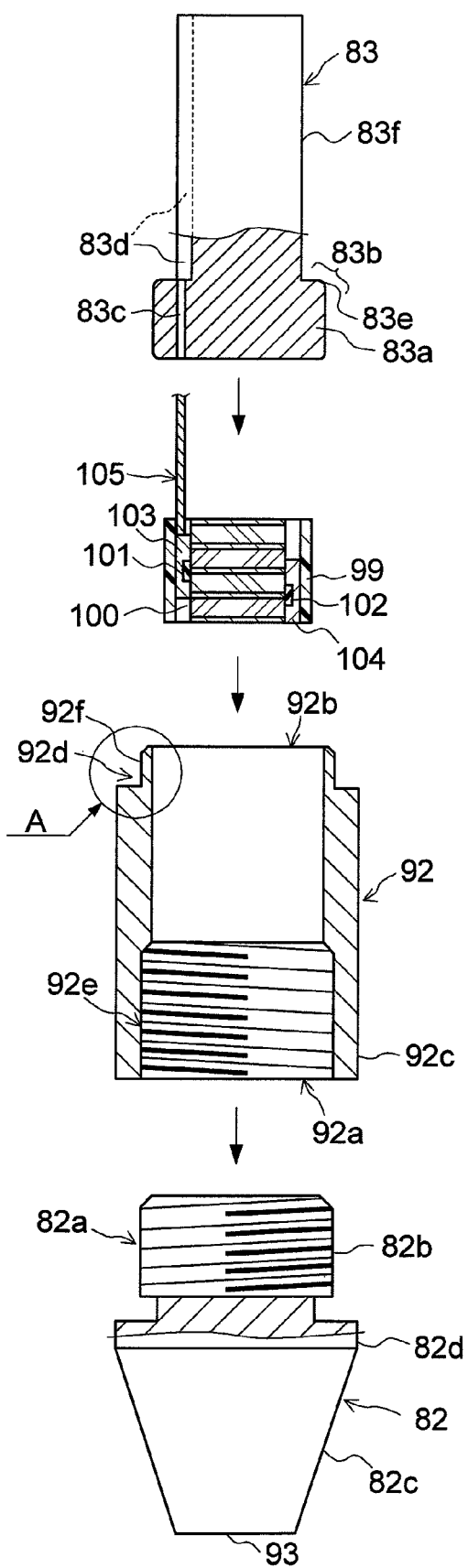
FIG. 10 is a front view showing in partially section the disassembled ultrasonic transducer of FIG. 9.
Figure 11:
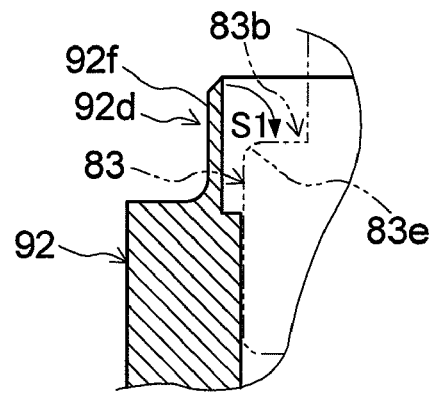
FIG. 11 is a detail view of a portion A of a side plate shown in FIG. 10.
Figure 12:
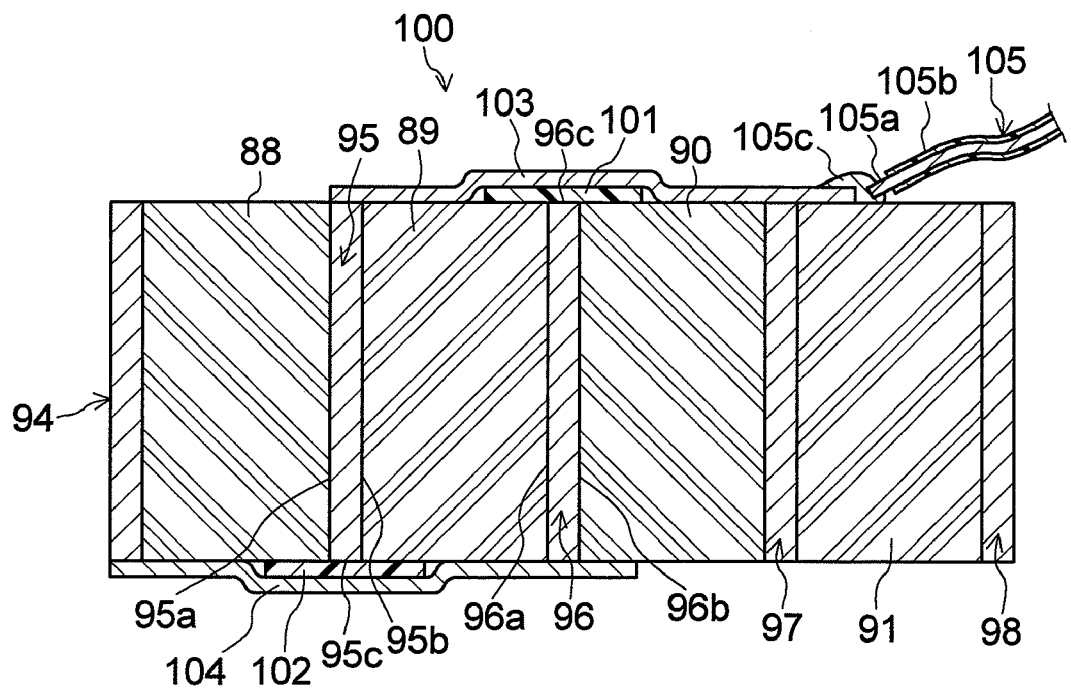
FIG. 12 is a sectional view showing a piezoelectric element unit incorporated in the ultrasonic transducer of FIG. 9.

Next, an eleventh embodiment of the invention will be described with reference to FIGS. 8 to 16. FIG. 8 is an exploded perspective view of an ultrasonic transducer 81 of the embodiment, FIG. 9 is a front view showing in partially section the ultrasonic transducer 81, FIG. 10 is a front view showing in partially section the disassembled ultrasonic transducer 81, FIG. 11 is a detail view of a portion A of a side plate 92 shown in FIG. 10, and FIG. 12 is a sectional view showing a piezoelectric element unit 100 incorporated in the ultrasonic transducer 81.

The ultrasonic transducer 81 of the embodiment is a Langevin type ultrasonic transducer which is used as a driving source of a handheld (handling type) ultrasonic device such as an ultrasonic cutter or an ultrasonic dental scaler. As shown in FIGS. 9 to 12, the ultrasonic transducer 81 is mainly configured by: the piezoelectric element unit 100 having piezoelectric elements 88, 89, 90, 91; a front plate 82 and back plate 83 which function as a pair of clamping members; and a side plate 92 which functions as a cover member.

The front plate 82 and the back plate 83 are configured as a columnar metal block in which titanium (Ti), a titanium alloy, stainless steel, or the like is used as a material. The side plate 92 is formed into a tubular shape (cylindrical shape) with using a material such as titanium, a titanium alloy, or stainless steel. As shown in FIG. 10, the piezoelectric elements 88 to 91 (the piezoelectric element unit 100) are clamped between the front plate 82 which is one clamping member, and the back plate 83 which is another clamping member.

Figure 9:
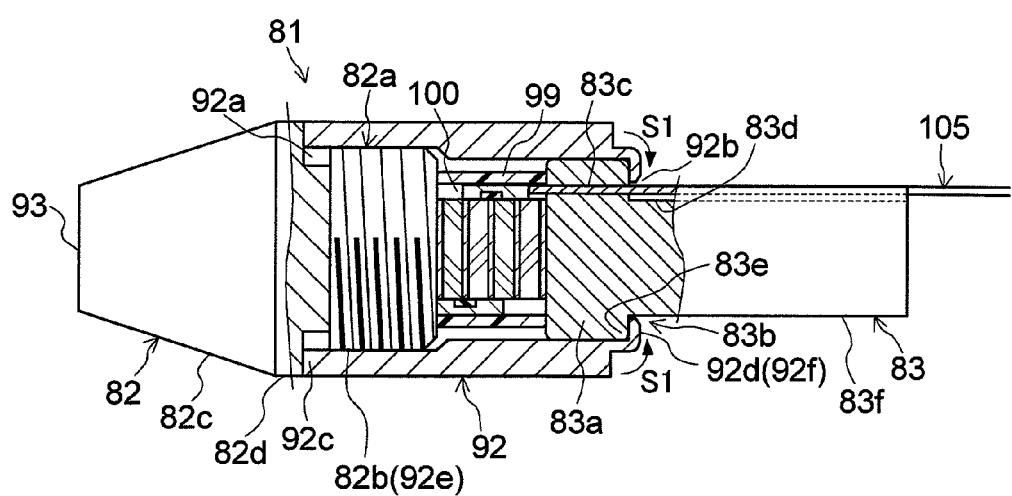
FIG. 9 is a front view showing in partially section the ultrasonic transducer of FIG. 8.

As shown in FIG. 9, the side plate 92 is crimped to at least one of the front plate 82 and the back plate 83 (in the embodiment, crimped to the back plate 83), in a state where the side plate cooperates with the front plate 82 and the back plate 83 to surround the piezoelectric element unit 100 having the piezoelectric elements 88 to 91.

The structure of the piezoelectric element unit 100 will be described. As shown in FIG. 12 (and FIGS. 9 and 10), the piezoelectric element unit 100 includes: the plurality of disk-like piezoelectric elements 88 to 91; positive terminal plates 95, 97 and negative terminal plates 94, 96, 98 which are disk-like electrode plates for the positive or negative electrode; insulating layers 101, 102, and conductive layers 103, 104. In the piezoelectric element unit 100, a plurality of electrode plates consisting of the positive terminal plates 95, 97 and the negative terminal plates 94, 96, 98, and the plurality of piezoelectric elements 88 to 91 are integrated with each other in an alternately stacked manner.

The positive terminal plates 95, 97 and the negative terminal plates 94, 96, 98 are formed so as to have, for example, a diameter of 4 mm and a thickness of 0.1 mm with using beryllium copper as a material. By contrast, each of the piezoelectric elements 88 to 91 is formed so as to have, for example, a diameter of 4 mm and a thickness of 1 mm, and an electrode layer which serves as a positive or negative electrode is formed on each of circular principal faces (both end faces). The piezoelectric elements 88 to 91 are produced by the following method. As a constituent material, lead zirconate titanate (PZT) is used. After press molding and sintering processes, a conductive paste is applied to each principal face, and a polarizing process in oil is performed to polarize the elements in the thickness direction. Thereafter, the elements are ground and polished so as to have a desired shape, and silver (Ag) is vapor-deposited on the principal faces, thereby forming the piezoelectric elements 88 to 91 having the electrode layers.

In the piezoelectric element unit 100, the piezoelectric elements are alternately stacked so that positional relationships of the positive and negative electrodes of adjacent piezoelectric elements are inverted. As described later, the electrodes of the piezoelectric elements are drawn out so that pairs of positive electrodes, and pairs of negative electrodes are respectively connected to each other as shown in FIG. 12, with the result that the plural piezoelectric elements 88 to 91 in the piezoelectric element unit 100 are electrically connected in parallel.

The piezoelectric elements 88 to 91 are not restricted to those produced by the above-described method. For example, from a planer piezoelectric element stock which is polarized in the thickness direction, a piezoelectric element having a desired shape may be cut out by a cutout process such as an ultrasonic process. Alternatively, a conductive paste is applied to each principal face (each end face) of an unsintered compact, and stacking and integrating processes are performed. Thereafter, sintering and polarizing processes are performed to obtain piezoelectric elements.

As shown in FIG. 12, the insulating layer 101 is formed so as to cover a part of a side face (the outer peripheral face of the negative terminal plate 96 exposed as an outer diameter portion of the piezoelectric element unit 100) 96c of the negative terminal plate 96. The insulating layer 102 is formed so as to cover a part of a side face 95c of the positive terminal plate 95. The insulating layers 101, 102 are configured by, for example, applying an electrically insulative insulating film, or applying and curing an insulating paste.

By contrast, as shown in FIG. 12, the conductive layer 103 connects (connects over the insulating layer 101) together the positive terminal plates 95, 97 which are adjacent to each other through the principal faces 96a, 96b of the negative terminal plate 96 and the piezoelectric elements 89, 90, from the outside of the insulating layer so as not to be short-circuited to the negative electrode. The conductive layer 104 connects together the negative terminal plates 94, 96 which are adjacent to each other through the principal faces 95a, 95b of the positive terminal plate 95 and the piezoelectric elements 88, 89, from the outside of the insulating layer 102 so as not to be short-circuited to the positive electrode. The conductive layers 103, 104 are configured by, for example, applying an electrically conductive film, or applying and curing an insulating paste. On the assumption that the use of grounding of the body (the front plate 82 and the back plate 83) of the ultrasonic transducer 81 is enabled, the negative terminal plate 96 and the negative electrode (electrode layer) of the body of the piezoelectric element 88 are connected to each other from the outside of the insulating layer 102 by the conductive layer 104, whereby the negative terminal plates 94, 98 at the both ends of the piezoelectric element unit 100 may be omitted. In this case, the component cost can be reduced.

In the piezoelectric element unit 100, as shown in FIG. 12 (and FIGS. 9 and 10), a lead wire 105 is connected to the conductive layer 103 which connects the positive terminal plates 95, 97 together. The lead wire 105 is configured by a covered wire in which a core wire 105a is covered by a covering layer 105b. One end portion of the core wire 105a of the lead wire 105 is connected to the conductive layer 103 through a connecting portion 105c which is formed by solidifying solder. As shown in FIGS. 9 and 10, the lead wire 105 is passed through a lead wire drawing out hole 83c formed in an insertion portion 83a (which will be described later) of the back plate 83, and drawn out (from the insides of the front plate 82, the back plate 83, and the side plate 92) to the outside of the ultrasonic transducer 81 through a cutaway portion 83d.

As shown in FIGS. 9 and 10, an electrically insulative short-circuit preventing layer 99 is interposed between: the body of the piezoelectric element unit 100 including the insulating layers 101, 102, the conductive layers 103, 104, the one end portion of the lead wire 105, and the connecting portion 105c of the wire; and the inner wall face of the cylindrical side plate 92 into which the body of the piezoelectric element unit 100 is to be housed. In an example of the method of forming the short-circuit preventing layer 99, an insulative coat or the like is applied to the inner wall face of the cylindrical side plate 92. Alternatively, the whole of a portion from which the positive electrode is exposed, and which is in the outer peripheral face of the piezoelectric element unit 100 including the side faces of the positive terminal plates 95, 97, the conductive layer 103, and the like may be covered by an insulating tape or a cured product of an insulating paste, whereby the short-circuit preventing layer 99 is formed.

Next, the structure of the body of the ultrasonic transducer 81 of the embodiment, the structures of the front plate 82, the back plate 83, and the side plate 92, and joining relationships between these members will be described in detail.

The ultrasonic transducer 81 of the embodiment is formed so as to have a total length which is substantially equal to 1/2 wavelength or 3/2 wavelength of the resonance frequency of the body of the ultrasonic transducer 81 (in the embodiment, for example, the total length of the ultrasonic transducer 81 is 31.3 mm).

In the front plate 82 which constitutes the forward end side of the ultrasonic transducer 81, a truncated conical shape portion 82c in which the forwardmost face (the smaller-diameter portion having a diameter of, for example, 5 mm) functions as a vibration radiating surface 93, a columnar portion 82d having a diameter which is equal to the larger-diameter portion (having a diameter of, for example, 10 mm) of the truncated conical shape portion 82c, and an insertion portion 82a on which a male thread 82b that is smaller in diameter than the columnar portion 82d is formed are continuously formed along the axial direction (vibration axis). The vicinity of the rear end face (basal end face) of the columnar portion 82d serves as the node position of the ultrasonic transducer 81 of the embodiment. The insertion portion 82a where the male thread 82b is formed in the peripheral face constitutes the basal end (rear end) portion of the front plate 82. The shape of the front plate 82 is not restricted to the above-described shape. For example, a plate in which the forward end side is formed into a columnar shape and the basal end side is formed into a truncated conical shape may be employed.

As shown in FIG. 10, the front plate 82 and the back plate 83 have the insertion portions 82a, 83a which are inserted from one and other opening portions 92a, 92b of the cylindrical side plate 92, so as to clamp the piezoelectric elements 88 to 91 which are placed inside the cylindrical side plate 92, respectively. A peripheral edge portion 92c of the one opening portion 92a of the cylindrical side plate 92 is screwed to the insertion portion 82a of the front plate 82. As shown in FIG. 10 (and FIG. 9), namely, a female thread 92e which is to be screwed with the male thread 82b of the front plate 82 is formed in the inner wall face that is in the side plate 92, and that includes the peripheral edge portion 92c of the one opening portion 92a.

By contrast, as shown in FIG. 9, a peripheral edge portion 92d of the other opening portion 92b of the cylindrical side plate 92 is crimped to the insertion portion 83a of the back plate 83. As shown in FIGS. 8 to 10, the back plate 83 is formed as a stepped columnar member. The rear end side (basal end side) of the plate is configured by a smaller-diameter columnar portion 83f, and the forward end side (on the side of the front plate 82) is configured by the larger-diameter insertion portion 83a. Therefore, the insertion portion 83a has a step portion 83b which includes an edge portion 83e in a boundary portion with respect to the columnar portion 83f. As shown in FIG. 10, the above-mentioned cutaway portion 83d is formed in an outer shape portion of the columnar portion 83f. In the insertion portion 83a, the above-mentioned lead wire drawing out hole 83c is opened on an extension of the cutaway portion 83d.

On the other hand, as shown in FIGS. 8 to 11, a thinned portion 92f in which the section of the body of the side plate 92 is formed to be thinner than the other portion) (a portion which is axially projected in a rib-like manner from a basal end portion of the side plate 92, and which has a thickness of 0.2 mm) is disposed in the peripheral edge portion 92d of the other opening portion 92b of the side plate 92.

As shown in FIG. 9, namely, the thinned portion 92f (the peripheral edge portion 92d of the opening portion 92b) of the side plate 92 is crimped to the step portion 83b including the edge portion 83e of the back plate 83, in a state where the piezoelectric element unit 100 having the piezoelectric elements 88 to 91 is surrounded (housed) by the side plate 92, and the piezoelectric elements 88 to 91 clamped between (the rearmost end face of the insertion portion 82a of) the front plate 82 and (the forwardmost face of the insertion portion 83a of) the back plate 83 are pressed at a pressure which is adjusted within a specific pressure range. Specifically, as shown in FIGS. 9 and 11, the thinned portion 92f is bent (plastically deformed) toward the inside of the cylindrical side plate 92 (in the direction of the arrow S1), so as to enfold the edge portion 83e of the step portion 83b of the back plate 83.

In the embodiment, as shown in FIG. 9, screwing is exemplified as the structure for joining the insertion portion 82a of the front plate 82 with the one opening portion 92a of the side plate 92. Alternatively, welding may be employed, and the front plate 82 and the side plate 92 may be integrally configured as a single member. With using a joining structure similar to the screwing and crimping structures which have been described above, it may be possible to configure an ultrasonic transducer in which the one opening portion 92a of the side plate 92 is crimped to the front plate 82 and the other opening portion 92b of the side plate 92 is screwed (or welded) to the back plate 83.

Figure 13:
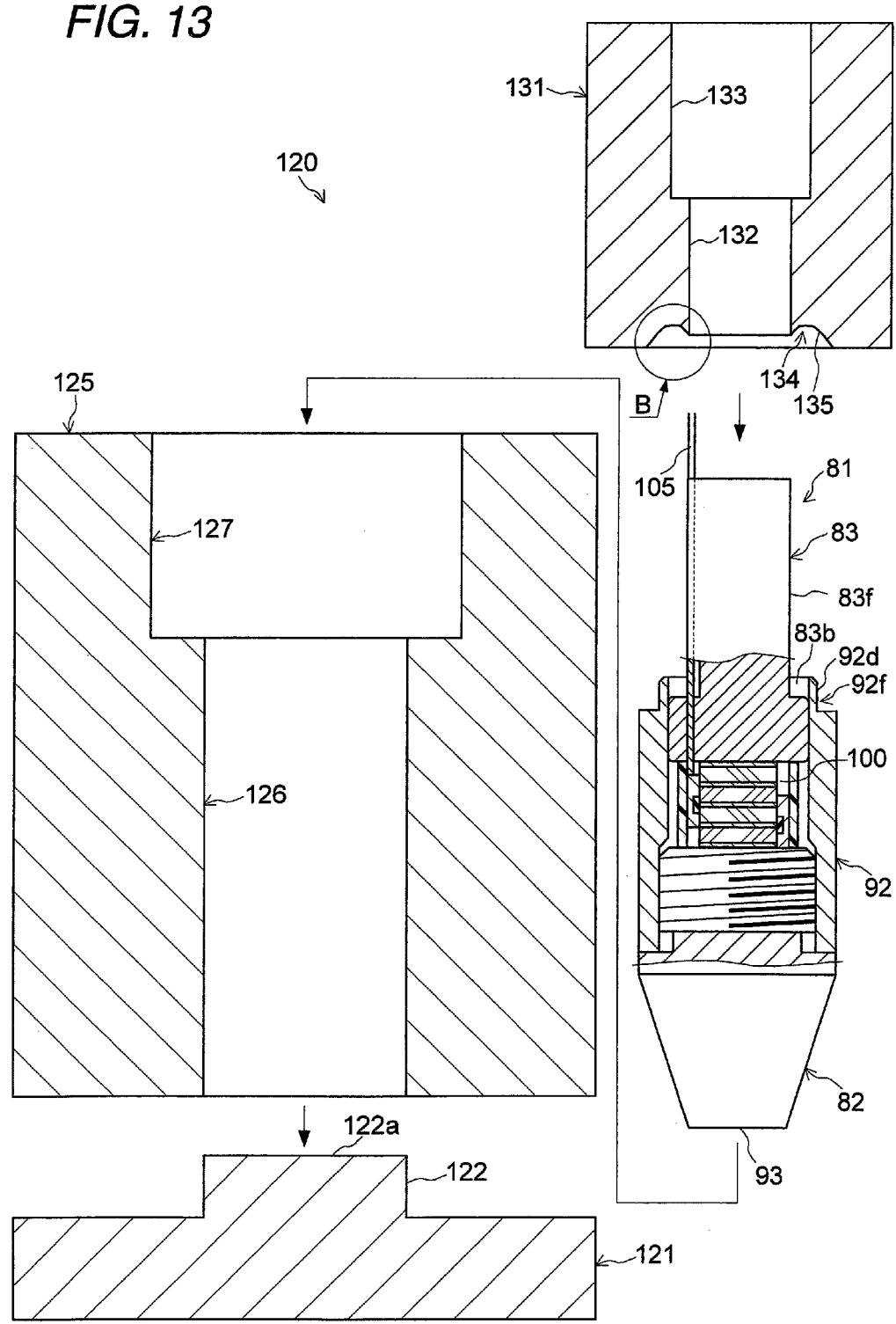
FIG. 13 is an exploded sectional view showing a crimping auxiliary apparatus which is used in production of the ultrasonic transducer of FIG. 9.

Next, a method of producing the ultrasonic transducer 81 having the above-described structure will be described with reference to FIGS. 13 to 16 in addition to FIGS. 8 to 12 which have been described above. FIG. 13 is an exploded sectional view showing a crimping auxiliary apparatus 120 which is used in production of the ultrasonic transducer 81, FIG. 14 is a detail view of a portion B of a pressing member 131 constituting the crimping auxiliary apparatus 120 of FIG. 13, FIG. 15 is a sectional view illustrating a crimping step in which the crimping auxiliary apparatus 120 is used, and FIG. 16 is a view illustrating the positional accuracy requested in the crimping auxiliary apparatus 120.

First, the structure of the crimping auxiliary apparatus 120 will be described. As shown in FIGS. 13 to 15, the crimping auxiliary apparatus 120 is configured by a base member 121, a guiding member 125, and the pressing member 131. The base member 121 is disposed on a working table in an environment for performing a crimping step of crimping the side plate 92 to the back plate 83. The base member 121 is configured as a planar stepped member, and includes a disk-like insertion convex portion 122 in an upper portion. The uppermost face of the insertion convex portion 122 functions as a butting face 122a against which the vibration radiating surface 93 of the ultrasonic transducer 81 is to butt, as shown in FIG. 15.

Figure 15:
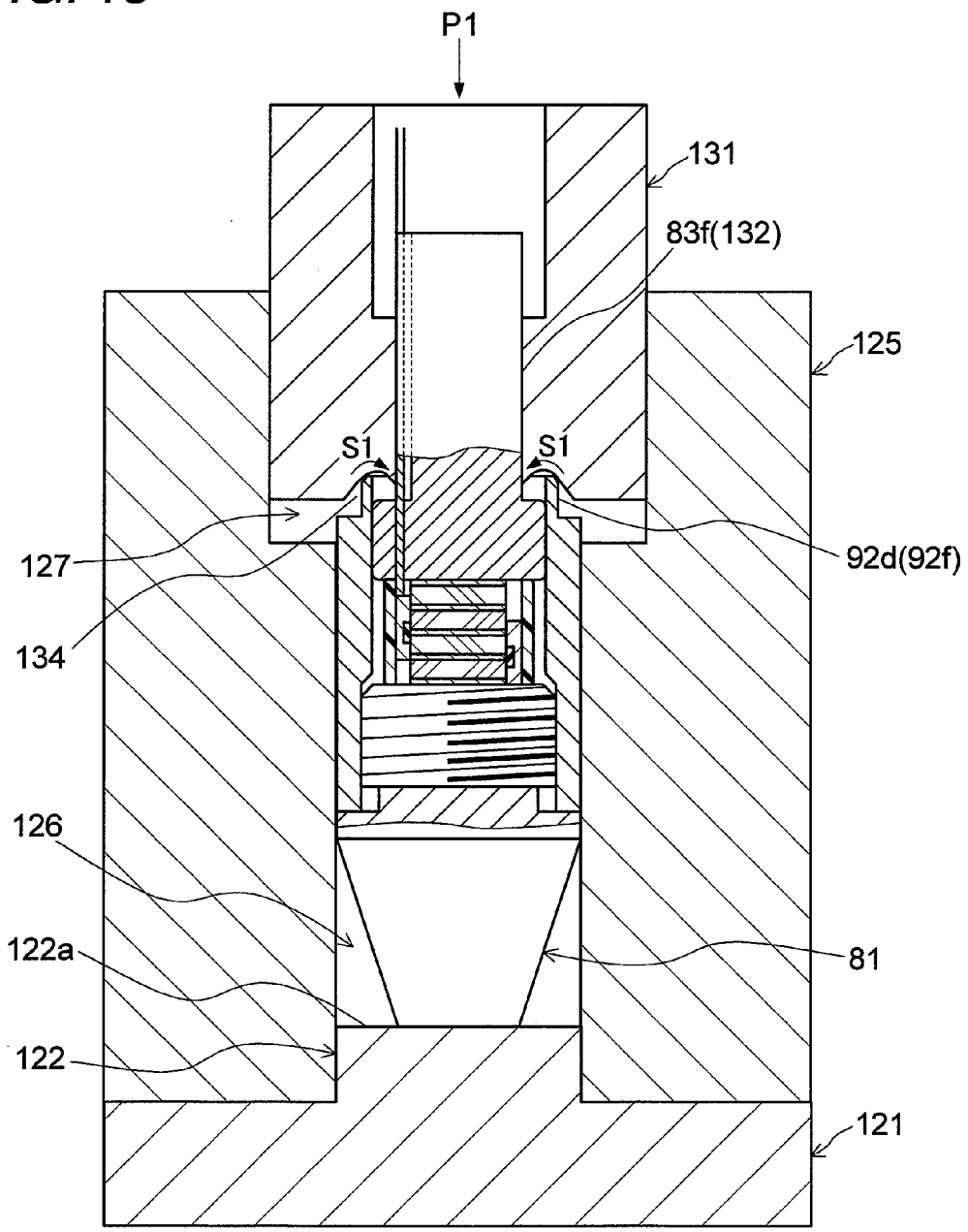
FIG. 15 is a sectional view illustrating a crimping step in which the crimping auxiliary apparatus of FIG. 13 is used.
Figure 16:
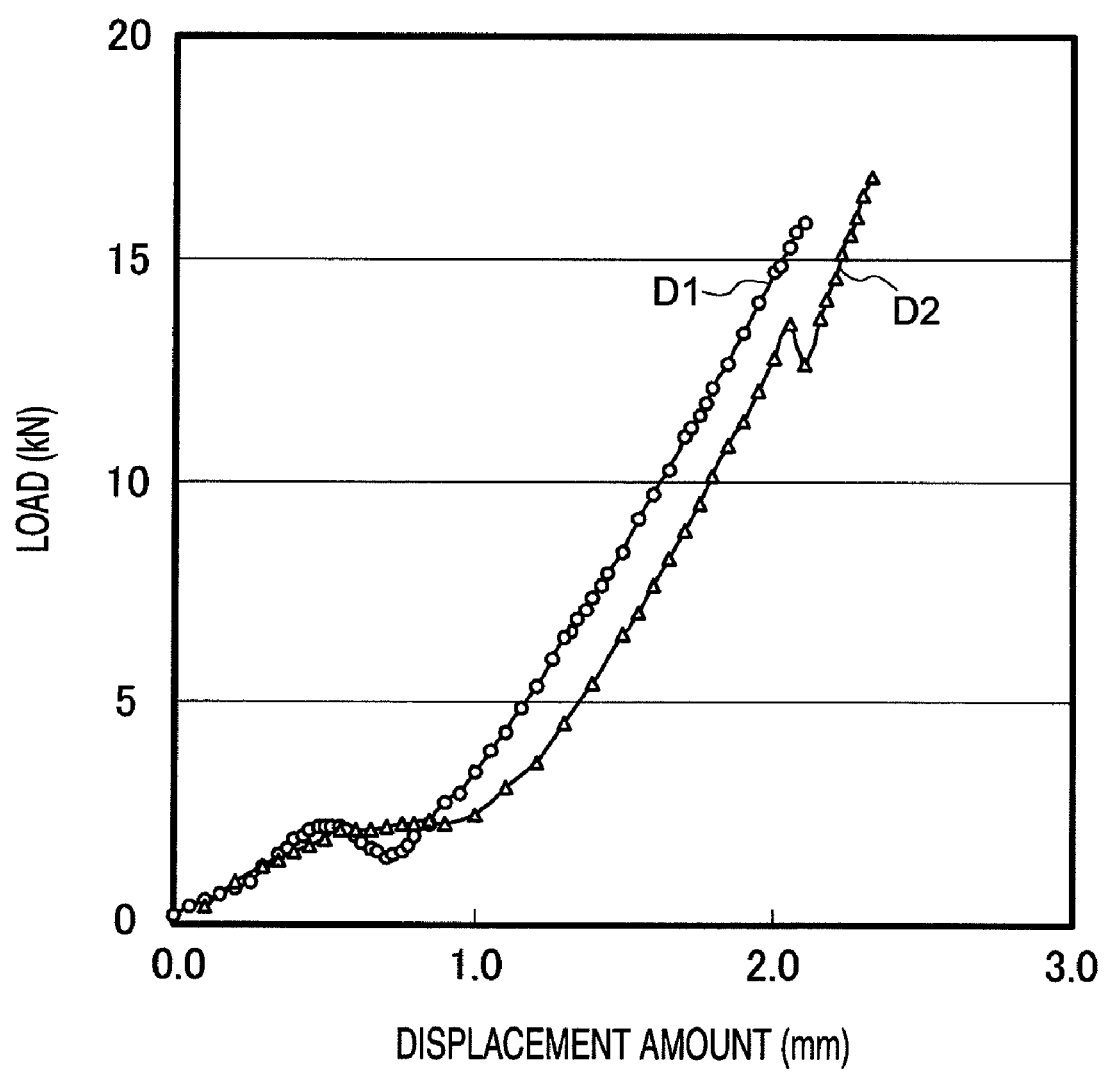
FIG. 16 is a view illustrating the positional accuracy requested in the crimping auxiliary apparatus of FIG. 13.

As shown in FIGS. 13 and 15, the guiding member 125 is formed into a cylindrical shape, and has a smaller-diameter side-plate positioning hole 126 and larger-diameter pressing member guiding hole 127 which are coaxially opened in a center portion. The side-plate positioning hole 126 is formed so as to be fitted to an outer diameter portion of the side plate 92 of the ultrasonic transducer 81, and that of the insertion convex portion 122 of the base member 121. The pressing member guiding hole 127 has a diameter which enables the hole to slide along an outer diameter portion of the pressing member 131 which is formed into a cylindrical shape, and, as shown in FIG. 15, guides the movement of the pressing member 131 which is lowered in the direction of the arrow P1 during the crimping process.

Figure 14:
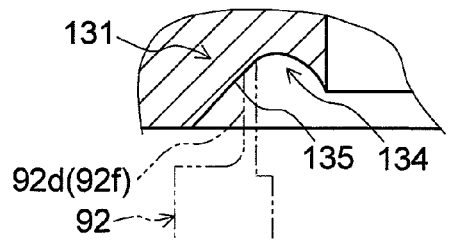
FIG. 14 is a detail view of a portion B of a pressing member constituting the crimping auxiliary apparatus of FIG. 13.

As shown in FIGS. 13 to 15, the pressing member 131 has: a through hole 133 through which the lead wire 105 and the back plate 83 are to be passed; a rear-plate positioning hole 132; and a crimping recess 134 having a pressing inclined face 135 which is inclined by, for example, 45° to the axial direction of the ultrasonic transducer 81. The rear-plate positioning hole 132 is fitted to the outer peripheral face of the columnar portion 83f of the back plate 83. As shown in FIGS. 14 and 15, the crimping recess 134 is an annular groove which is configured so that the pressing inclined face 135 and the thinned portion 92f are opposed to each other in a state where the ultrasonic transducer 81 is set in the side-plate positioning hole 126 of the guiding member 125 placed on the base member 121, and the pressing member 131 is inserted into the pressing member guiding hole 127.

In a state where the ultrasonic transducer 81 is set in the crimping auxiliary apparatus 120, as shown in FIGS. 14 and 15, the pressing inclined face 135 and (the most basal end portion of) the thinned portion 92f are opposed to each other, and, when the pressing member 131 is lowered in the direction of the arrow P1, a pressing force is applied in a direction along which the pressing inclined face 135 bends the thinned portion 92f toward the inner side of the cylindrical side plate 92 (in the direction of the arrow S1), whereby crimping is performed.

In FIG. 16, D1 indicates data in the case where, when the pressing member 131 is lowered in the direction of the arrow P1, the thinned portion 92f buckles, and D2 indicates data in the case where, when the pressing member 131 is lowered in the direction of the arrow P1, the thinned portion 92f is adequately bent in the direction of the arrow S1 so as to enfold the edge portion 83e of the step portion 83b of the back plate 83. From FIG. 16, it will be seen that, during the process of deforming the thinned portion 92f, the load with respect to the displacement of the pressing member 131 is temporarily relaxed. When buckling occurs, the increase of the load with respect to the displacement is slightly enlarged.

More specifically, in a state where a curved portion of the crimping recess 134 which is outside the pressing inclined face 135 is opposed to (the most basal end portion of) the thinned portion 92f, when the pressing member 131 is lowered in the direction of the arrow P1, the thinned portion 92f buckles (the thinned portion 92f is not adequately bent in the direction of the arrow S1), and hence a desired crimping strength is hardly obtained. The base member 121, the guiding member 125, and the pressing member 131 are formed at a component accuracy which can avoid such a situation.

Next, an actual method by which the ultrasonic transducer 81 is produced, and which uses the crimping auxiliary apparatus 120 will be described.

First, while placing the front plate 82 and the back plate 83 are placed at a position where the piezoelectric element unit 100 shown in FIG. 12 including the piezoelectric elements 88 to 91 is clamped from the both sides, the side plate 92 is placed at a position where it cooperates with the front plate 82 and the back plate 83 to surround the piezoelectric element unit 100. As shown in FIG. 10, specifically, the peripheral edge portion 92c of the one opening portion 92a of the side plate 92 is screwed to the insertion portion 82a of the front plate 82 in a state where the plate is inserted from the one opening portion 92a into the side plate 92. The piezoelectric element unit 100 is inserted (housed) from the other opening portion 92b into the cylindrical side plate 92 screwed to the front plate 82. In this case, before the piezoelectric element unit 100 is housed, the short-circuit preventing layer 99 which electrically insulates the piezoelectric element unit 100 from the side plate 92 is previously formed.

Then, the insertion portion 83a of the back plate 83 is inserted from the other opening portion 92b into the side plate 92 so as to clamp the piezoelectric element unit 100 inserted into the cylindrical side plate 92, between the back plate and the insertion portion 82a of the front plate 82. In this case, the lead wire 105 connected to the piezoelectric element unit 100 is drawn out to the outside through the lead wire drawing out hole 83c of the back plate 83 and the cutaway portion 83d.

Then, (a semifinished product of) the ultrasonic transducer 81 including the piezoelectric element unit 100, front plate 82, back plate 83, and side plate 92 which are installed as described above is set in the crimping auxiliary apparatus 120 as shown in FIG. 15. With using an apparatus which can apply compressive stress, such as a strength testing apparatus (autograph) or a pressing apparatus, the pressing member 131 is uniaxially pressed at a constant rate (for example, 0.5 mm/min) in the direction of the arrow P1, and the thinned portion 92f of the side plate 92 is plastically deformed (crimped) in the direction of the arrow S1 so as to enfold the edge portion 83e of the step portion 83b of the back plate 83.

In the crimping step, ultrasonic crimping in which the to-be-crimped portion (the thinned portion 92f) is plastically deformed by pressurization using ultrasonic vibration is employed. In the ultrasonic crimping, the pressing force can be finely divided and efficiently transmitted to the thinned portion 92f, and hence it is possible to obtain high crimping strength. In the crimping step, the crimping process is performed while the clamping force which is applied from the front plate 82 and the back plate 83 to the piezoelectric elements 88 to 91 is variably changed (the axial distance between the front plate 82 and the back plate 83 is variably changed), and the output from the piezoelectric elements which is varied in accordance with the change of the clamping force is monitored (for example, the electrostatic capacitance is checked). Namely, crimping is performed in such a manner that, the back plate 83 is fixed to the position where a predetermined output value is obtained from the piezoelectric elements.

Specifically, the variable adjustment (the adjustment of the electrostatic capacitance) of the clamping force which is applied from the front plate 82 and the back plate 83 to the piezoelectric elements 88 to 91 is performed in order to obtain desired vibration characteristics form the body of the ultrasonic transducer 81. Namely, the ultrasonic transducer 81 has the resonance frequency which is physically determined mainly by the structure, and a property that the transducer vibrates most efficiently in the case where a driving signal corresponding to the resonance frequency is given. Usually, an equivalent circuit in the vicinity of the resonance frequency is expressed by connecting in parallel a damping capacitance component (Cd) configured by the piezoelectric element unit 100 including the piezoelectric elements 88 to 91 and the positive and negative terminal plates 94 to 98, to a series resonance circuit indicated by the resonance component which is a characteristic of mechanical vibrations, and which is configured by an inductance component (L) and a capacitance component (C), and the resistance component which indicates a mechanical load.

In the method of producing the ultrasonic transducer 81 of the embodiment, in order to drive the ultrasonic transducer 81 at the above-mentioned resonance frequency, therefore, the clamping force applied to the piezoelectric element unit 100 is adjusted as tuning for matching the damping capacitance component (Cd) indicating the electrostatic capacitance of the ultrasonic transducer 81, to a predetermined designed value.

As described above, in the ultrasonic transducer 81 of the embodiment, the piezoelectric element unit 100 is housed in the side plate 92 which is previously installed with the front plate 82, and, in this state, the back plate 83 is crimped to the side plate 92 without applying torsional stress to the piezoelectric elements 88 to 91, thereby completing the installing process. In the ultrasonic transducer 81, therefore, the piezoelectric elements can be installed by an adequate holding force while suppressing positional deviation during installation of the piezoelectric elements. Consequently, the vibration characteristics of the ultrasonic transducer can be prevented from being dispersed, and mechanical stress which is relatively large can be suppressed from being applied to the piezoelectric elements. In the ultrasonic transducer 81 of the embodiment, moreover, crimp rings are not necessary unlike the above-described first and fourth to ninth embodiments. Therefore, the number of components can be reduced, and the production steps can be simplified.

Although the first aspect of the invention has been specifically described with reference to the first, third, fourth, fifth, ninth, and eleventh embodiments, the first aspect of the invention is not restricted to these embodiments, and may be variously modified without departing the spirit. In the embodiments in which the crimp rings are used, for example, a titanium alloy has been exemplified as the material of the front plate, the back plate, and the side plate. Alternatively, stainless steel or the like may be used as the material. In the first, third, fourth, fifth, and ninth embodiments excepting the eleventh embodiment, the node position (the position of a vibration node) of the ultrasonic transducer has not been particularly described. Preferably, the ultrasonic transducer is configured so that a to-be-crimped portion which is low in mechanical strength in the whole of the ultrasonic transducer is at the node position.

Although the second aspect of the invention has been specifically described with reference to the second, sixth, seventh, eighth, and tenth embodiments, the second aspect of the invention is not restricted to these embodiments, and may be variously modified without departing the spirit. In the above-mentioned embodiments, for example, a titanium alloy has been exemplified as the material of the front plate, the back plate, and the side plate. Alternatively, stainless steel, duralumine, or the like may be used as the material. In the above-mentioned embodiments, the node position (the position of a vibration node) of the ultrasonic transducer has not been particularly described. Preferably, the ultrasonic transducer is configured so that a welded portion (the welded portions 5a, 6a or the to-be-welded portions 35, 36) which is relatively low in strength in the whole of the ultrasonic transducer is at the node position.

What is claimed is:

1. An ultrasonic transducer comprising:
   piezoelectric elements;
   a pair of clamping members which clamp said piezoelectric elements; and
   a cover member which is crimped to at least one of said pair of clamping members in a state where said cover member cooperates with said pair of clamping members to surround said piezoelectric elements,
   wherein said cover member is configured into a cylindrical shape, said pair of clamping members have insertion portions which are inserted from one and other opening portions of said cylindrical cover member to clamp said piezoelectric elements placed inside said cylindrical cover member, respectively, and
   wherein peripheral edge portions of said opening portions of said cylindrical cover member are crimped to said insertion portions of said pair of clamping members, respectively.

2. The ultrasonic transducer according to claim 1, wherein said crimping is performed in a state where said piezoelectric elements are pressed by said pair of clamping members.

3. The ultrasonic transducer according to claim 2, wherein said crimping is performed in a state where said piezoelectric elements clamped by said pair of clamping members are pressed at a pressure which is adjusted within a pressure range.

4. The ultrasonic transducer according to claim 1, wherein said cylindrical cover member is crimped through annular engaging members into which said peripheral edge portions of said cover member are inserted, respectively.

5. The ultrasonic transducer according to claim 1, wherein said cover member and one of said clamping members are monolithic.

6. The ultrasonic transducer according to claim 1, wherein said ultrasonic transducer further comprises a buffer member that is fixed to at least one of said clamping members, and that is lower in hardness than said clamping member to which said buffer member is fixed.

7. The ultrasonic transducer according to claim 1, wherein said cover member is configured into a cylindrical shape, said pair of clamping members have insertion portions which are inserted from one and other opening portions of said cylindrical cover member to clamp said piezoelectric elements placed inside said cylindrical cover member, respectively,
   a peripheral edge portion of said one opening portion of said cylindrical cover member is screwed or welded to said insertion portion of said one clamping member, and
   a peripheral edge portion of said other opening portion of said cylindrical cover member is crimped to said insertion portion of said other clamping member.

8. The ultrasonic transducer according to claim 7, wherein said insertion portion of said other clamping member comprises a step portion, and
   said peripheral edge portion of said other opening portion of said cylindrical cover member is crimped to said step portion.

9. An ultrasonic transducer comprising:
   piezoelectric elements;
   at least one pair of clamping members which clamp said piezoelectric elements; and
   a cover member which is welded to at least one of said pair of clamping members while surrounding said piezoelectric elements interposed between said at least one pair of clamping members,
   wherein said cover member is configured into a cylindrical shape, said pair of clamping members have insertion portions which are inserted from one and other opening portions of said cylindrical cover member to clamp said piezoelectric elements placed inside said cylindrical cover member, respectively, and
   wherein peripheral edge portions of said opening portions of said cylindrical cover member are crimped to said insertion portions of said pair of clamping members, respectively.

10. The ultrasonic transducer according to claim 9, wherein said cover member and one of said clamping members are monolithic.

11. The ultrasonic transducer according to claim 10, wherein said welding is performed in a state where said piezoelectric elements are pressed by said pair of clamping members.

12. The ultrasonic transducer according to claim 9, wherein laser welding or electric welding is employed as said welding.

13. The ultrasonic transducer according to claim 12, wherein rib-like projections are provided in to-be-welded portions where said electric welding is to be performed.

14. The ultrasonic transducer according to claim 9, wherein said ultrasonic transducer further comprises a buffer member that is fixed to at least one of said clamping members, and that is lower in hardness than said clamping member to which said buffer member is fixed.

* * * * *